(12) United States Patent
Daugherty et al.

(10) Patent No.: US 10,640,762 B2
(45) Date of Patent: *May 5, 2020

(54) METHODS FOR ENHANCING BACTERIAL CELL DISPLAY OF PROTEINS AND PEPTIDES

(71) Applicant: The Regents of the University of California, Oakland, CA (US)

(72) Inventors: Patrick Sean Daugherty, Santa Barbara, CA (US); Jeffrey Rice, Goleta, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/613,877

(22) Filed: Jun. 5, 2017

(65) Prior Publication Data

US 2018/0002687 A1 Jan. 4, 2018

Related U.S. Application Data

(63) Continuation of application No. 14/717,679, filed on May 20, 2015, now Pat. No. 9,695,415, which is a continuation of application No. 13/615,072, filed on Sep. 13, 2012, now Pat. No. 9,062,107, which is a continuation of application No. 12/220,448, filed on Jul. 24, 2008, now Pat. No. 8,293,685.

(60) Provisional application No. 60/962,086, filed on Jul. 26, 2007.

(51) Int. Cl.
*C12N 15/10* (2006.01)
*C07K 14/195* (2006.01)
*C12N 15/00* (2006.01)
*C07K 14/245* (2006.01)

(52) U.S. Cl.
CPC ........ *C12N 15/1037* (2013.01); *C07K 14/195* (2013.01); *C07K 14/245* (2013.01); *C12N 15/00* (2013.01); *C07K 2319/00* (2013.01)

(58) Field of Classification Search
CPC .......................... C12N 15/1037; C07K 14/195
See application file for complete search history.

(56) References Cited

U.S. PATENT DOCUMENTS

| | | | |
|---|---|---|---|
| 3,817,837 A | 6/1974 | Rubenstein et al. | |
| 3,850,752 A | 11/1974 | Schuurs et al. | |
| 3,939,350 A | 2/1976 | Kronick et al. | |
| 3,996,345 A | 12/1976 | Ullman et al. | |
| 4,275,149 A | 6/1981 | Litman et al. | |
| 4,277,437 A | 7/1981 | Maggio | |
| 4,366,241 A | 12/1982 | Tom et al. | |
| 4,399,216 A | 8/1983 | Axel et al. | |
| 4,551,433 A | 11/1985 | DeBoer | |
| 4,560,655 A | 12/1985 | Baker | |
| 4,657,866 A | 4/1987 | Kumar | |
| 4,767,704 A | 8/1988 | Cleveland et al. | |
| 4,927,762 A | 5/1990 | Darfler | |
| 5,571,698 A | 11/1996 | Ladner et al. | |
| 5,962,255 A | 10/1999 | Griffiths et al. | |
| 5,977,301 A | 11/1999 | Zuckerman et al. | |
| 5,990,275 A | 11/1999 | Whitlow et al. | |
| 6,300,065 B1 | 10/2001 | Kieke et al. | |
| 6,303,344 B1 | 10/2001 | Patten et al. | |
| 6,423,538 B1 | 7/2002 | Wittrup et al. | |
| 6,492,160 B1 | 12/2002 | Griffiths et al. | |
| 6,548,249 B1 | 4/2003 | Anderson et al. | |
| 6,660,257 B1 | 12/2003 | McWherter et al. | |
| 6,660,843 B1 | 12/2003 | Feige et al. | |
| 6,696,251 B1 | 2/2004 | Wittrup et al. | |
| 6,699,658 B1 | 3/2004 | Wittrup et al. | |
| 6,723,512 B2 | 4/2004 | Larocca et al. | |
| 7,256,038 B2* | 8/2007 | Daugherty ......... | C12N 15/1044 435/320.1 |
| 7,612,019 B2* | 11/2009 | Daugherty ......... | C12N 15/1044 506/9 |
| 7,666,817 B2 | 2/2010 | Daugherty et al. | |
| 8,293,685 B2* | 10/2012 | Daugherty ........... | C07K 14/245 506/14 |
| 8,361,933 B2* | 1/2013 | Daugherty ......... | C12N 15/1044 506/14 |
| 9,062,107 B2* | 6/2015 | Daugherty ........... | C07K 14/245 |
| 9,121,828 B2* | 9/2015 | Daugherty ......... | C12N 15/1037 |
| 9,134,309 B2* | 9/2015 | Daugherty ......... | C12N 15/1044 |
| 9,234,847 B2* | 1/2016 | Daugherty ......... | C12N 15/1037 |
| 9,309,510 B2 | 4/2016 | La Porte et al. | |

(Continued)

FOREIGN PATENT DOCUMENTS

| | | |
|---|---|---|
| EP | 0036776 | 9/1981 |
| EP | 0474891 | 3/1992 |

(Continued)

OTHER PUBLICATIONS

Ahmed, et al. (2006) "Vascular Endothelial Growth Factor (VEGF) Inhibition by Small Molecules" *J. Chemother.* 16(Suppl. 4):59-63.
Ascheim, et al., "Clipping away at protease substrates, *Nature Biothnology*"; vol. 24, No. 6, (2006) pp. 665.
Baird, et al. (1999) "Circular Permutation and Receptor Insertion within Green Fluorescent Proteins" *Proc. Natl. Acad. Sci. U.S.A.* 96(20):11241-11246.
Beebe, et al. (2003) "Pharmacological Characterization of CP-547,632, a Novel Vascular Endothelial Growth Factor Receptor-2 Tyrosine Kinase Inhibitor for Cancer Therapy"; *Cancer Res.* 63(21):7301-7309.
Bergsland, et al. (2004) "Vascular Endothelial Growth Factor as a Therapeutic Target in Cancer"; *Am. J. Health Syst. Pharm.* 61(21 Suppl. 5):S4-S11.

(Continued)

*Primary Examiner* — Amber D Steele
(74) *Attorney, Agent, or Firm* — Edward J. Baba; Bozicevic, Field & Francis LLP

(57) ABSTRACT

Methods of making and using bacterial display polypeptide libraries using circularly permuted OmpX (CPX) variants are disclosed. The invention further relates to methods for enhancing the display of proteins and peptides at the surface of bacteria by optimizing linkers and incorporating mutations at positions 165 and 166 of CPX.

39 Claims, 4 Drawing Sheets
Specification includes a Sequence Listing.

(56) References Cited

U.S. PATENT DOCUMENTS

| | | | |
|---|---|---|---|
| 9,695,415 B2* | 7/2017 | Daugherty | C07K 14/245 |
| 10,017,757 B2* | 7/2018 | Daugherty | C12N 15/1037 |
| 10,041,063 B2* | 8/2018 | Daugherty | C12N 15/1044 |
| 2003/0013150 A1 | 1/2003 | Manosroi et al. | |
| 2003/0049729 A1 | 3/2003 | Manosroi et al. | |
| 2003/0082575 A1 | 5/2003 | Schultz et al. | |
| 2004/0146976 A1 | 7/2004 | Wittrup et al. | |
| 2005/0047461 A1 | 3/2005 | Kihara et al. | |
| 2005/0196406 A1 | 9/2005 | Daugherty et al. | |
| 2006/0003387 A1 | 1/2006 | Peelle et al. | |
| 2006/0029947 A1 | 2/2006 | Georgiou et al. | |
| 2007/0020678 A1 | 1/2007 | Ault-Riche et al. | |
| 2007/0065878 A1 | 3/2007 | Daugherty et al. | |
| 2007/0099247 A1 | 5/2007 | Daugherty et al. | |
| 2007/0099267 A1 | 5/2007 | Harvey et al. | |
| 2009/0035317 A1 | 2/2009 | Daugherty et al. | |
| 2009/0062142 A1 | 3/2009 | Daugherty et al. | |
| 2010/0113303 A1 | 5/2010 | Daugherty et al. | |
| 2010/0173349 A1 | 7/2010 | Daugherty et al. | |
| 2013/0123141 A1 | 5/2013 | Daugherty et al. | |
| 2013/0210673 A1 | 8/2013 | Daugherty et al. | |
| 2014/0235467 A1 | 8/2014 | La Porte et al. | |
| 2015/0031855 A1 | 1/2015 | Daugherty et al. | |
| 2016/0010084 A1 | 1/2016 | Daugherty et al. | |
| 2016/0032279 A1 | 2/2016 | Daugherty et al. | |
| 2016/0264961 A1 | 9/2016 | La Porte et al. | |
| 2019/0032043 A1 | 1/2019 | Daugherty et al. | |
| 2019/0264194 A1 | 8/2019 | Daugherty et al. | |

FOREIGN PATENT DOCUMENTS

| | | |
|---|---|---|
| EP | 0474894 | 3/1992 |
| EP | 0922957 | 6/1999 |
| WO | WO 1990003430 | 4/1990 |
| WO | WO 1998017810 | 4/1998 |
| WO | WO 2005047461 | 5/2005 |
| WO | WO 2007027935 | 3/2007 |
| WO | WO 2009014726 | 1/2009 |
| WO | WO 2009025846 | 2/2009 |
| WO | WO 2010081173 | 7/2010 |
| WO | WO 2010096838 | 8/2010 |
| WO | WO 2014026136 | 2/2014 |

OTHER PUBLICATIONS

Bessette, et al., "Flow Cytometric Screening of cDNA Expression Libraries for Fluorescent Proteins"; *Biotechnology Progress*, vol. 20, Issue 3, pp. 963-967 (2004).

Bessette, et al., "Rapid isolation of high-affinity protein binding peptides using bacterial display"; *Protein Engineering, Design and Selection* 17 (10) (2004):731-739.

Beutler, et al. (2000) "Folding and Activity of Circularly Permuted Forms of a Polytopic Membrane Protein"; *Proc. Natl. Acad. Sci. USA* 97(4):1477-1482.

Boder, et al. (1997) "Yeast Surface Display for Screening Combinational Polypeptide Libraries"; *Nat. Biotechnol.* 15(6):553-557.

Boder, et al. (1998) "Optimal Screening of Surface-Displayed Polypeptide Libraries"; *Biotechnol. Prog.* 14(1):55-62.

Boder, et al. (2000) "Directed Evolution of Antibody Fragments with Monovalent Femtomolar Antigen-Binding Affinity"; *PNAS USA* 97(20):10701-10705.

Bos & Tommassen (2004) "Biogenesis of the Gram-negative bacterial outer membrane"; *Curr Opin Microbiol* 7(6):610-616.

Bos, et al. (2004) "Biogenesis of the Gram-Negative Bacterial Outer Membrane"; *Annu. Rev. Microbiol.* 61:191-214.

Boulware, et al. (2006) "Protease specificity determination by using cellular libraries of peptide substrates (CLiPS)"; *Proc Natl Acad Sci U S A* 103(20):7583-7588.

Bupp, et al. (2002) "Altering Retroviral Tropism Using a Random-Display Envelope Library"; *Mol. Ther.* 5(3):329-335.

Camaj, et al., "Ligand-mediated protection against phage lysis as a positive selection strategy for the enrichment of epitopes displayed on the surface of *E. coli* cells"; *Biol Chem.* 382(12); Dec. 2001:1669-1677.

Caponigro, et al. (2005) "New Drugs in Cancer Therapy, National Tumor Institute, Naples, Jun. 17-18, 2004"; *Anticancer Drugs* 16(2):211-221.

Charbit, et al. (1986) "Probing the Topology of a Bacterial Membrane Protein by Genetic Insertion of a Foreign Epitope: Expression at the Cell Surface"; *EMBO J* 5 (11):3029-3037.

Choo & Klug (1995) "Designing DNA-binding proteins on the surface of filamentous phage"; *Current Opinion in Biotechnology* 6(4):431-436.

Christmann, et al. (1999) "The Cystine Knot of a Squash-Type Protease Inhibitor as a Structural Scaffold for *Escherichia coli* Cell Surface Display of Conformationally Constrained Peptides"; *Protein Eng* 12(9):797-806.

Ciafré, et al. (2004) "An Anti-VEGF Ribozyme Embedded within the Adenoviral VAI Sequence Inhibits Glioblastoma Cell Angiogenic Potential in Vitro"; *J. Vasc. Res.* 41(3):220-228.

Cunningham, et al. (1979) "Favin versus Concanavalin A: Circularly Permuted Amino Acid Sequences"; *Proc. Natl. Acad. Sci. U.S.A.* 76(7):3218-3222.

Dane, et al. (2006) "Isolation of Cell Specific Peptide Ligands Using Fluorescent Bacterial Display Libraries"; *J. Immunol. Methods* 309(1-2):120-129.

Daugherty, et al. (2000) "Quantitative Analysis of the Effect of the Mutation Frequency on the Affinity Maturation of Single Chain Fv Antibodies" *PNAS USA* 97(5):2029-2034.

Daugherty, et al. (1999) "Development of an optimized expression system for the screening of antibody libraries displayed on the *Escherichia coli* surface"; *Protein Eng.* 12 (7): 613-621.

Daugherty, et al., "Flow cytometric screening of cell-based libraries"; *Journal of Immunological Methods* vol. 243, Issues 1-2, Sep. 21, 2000, pp. 211-227.

Daugherty, et al., "Protein engineering with bacterial display"; *Curr Opin Struct Biol.* 17(4); Aug. 2007:474-480.

Daugherty, et al., "Sorting out the best targets"; *Nature Methods* 3, No. 7, p. 498 (2006).

Deperthes, D, "Phage display substrate: a blind method for determining protease specificity"; *Biol Chem.* 383(7-8): Jul.-Aug. 2002:1107-1112.

Eisenstein, M. (2006) "Sorting Out the Best Targets"; *Nature Methods*, 3(7):498.

EPO Search Report: EP Supplementary Partial EPO Search Report for EP 0416813.2 dated Nov. 2, 2006; EPO Form 1507.2.

EPO Search Report: Supplementary EPO Search Report for EP 04816813.2 dated Jan. 30, 2007; EPO Form 1507.2.

Etz, et al., "Bacterial phage receptors, versatile tools for display of polypeptides on the cell surface"; *Journal of Bacteriology*, vol. 183, No. 23; Dec. 2001; p. 6924-6935.

Feldhaus, et al. (2003) "Flow-Cytometric Isolation of Human Antibodies From a Nonimmune *Saccharomyces cerevisiae* Surface Display Library"; *Nat. Biotechnol.* 21(2):163-170.

Fernandez, et al., "Solution NMR studies of the integral membrane proteins OmpX and OmpA from *Escherichia coli*"; *FEBS Lett.* 504(3); Aug. 31, 2001:173-178.

Fields, et al. (1994) "The Two-Hybrid System: An Assay for Protein-Protein Interactions"; *Trends in Genetics* 10(8):286-292.

Francisco, et al. (1992) "Transport and Anchoring of Beta Lactamase to the External Surface. of *Escherichia coli*"; *PNAS USA* 89(7);2713-2717.

Francisco, et al. (1993) "Production and Fluoresence-Activated Cell Sorting of *Escherichia coli* Expressing a Functional Antibody Fragment Antibody Fragment on the External Surface"; *Proc. Natl. Acad. Sci. U.S.A.* 90(22):10444-10448.

Freud L,"Insertion of peptides into cell-surface-exposed areas of the *Escherichia coli* OmpA protein does not interfere with export and membrane assembly"; *Gene.* 82(2); Oct. 30, 1989:229-236.

Gao, et al. (2002) "Down-Regulation of Vascular Endothelial Growth Factor and Up-Regulation of Pigment Epithelium-Derived Factor: A Possible Mechanism for the Anti-Angiogenic Activity of Plasminogen Kringle 5"; *J. Biol. Chem.* 277(11):9492-9497.

(56) References Cited

OTHER PUBLICATIONS

Garrett, et al. (2003) "Effect of Linker Sequence on the Stability of Circularly Permuted Variants of Ribonuclease T1"; *Bioorg. Chem.* 31(5):412-424.
Georgiou (2000) "Analysis of Large Libraries of Protein Mutants Using Flow Cytometry"; *Adv. Protein Chem.* 55:293-315.
Georgiou, et al. (1997) "Display of Heterologous Proteins on the Surface of Microorganisms: From the Screening of Combinatorial Libraries to Live Recombinant Vaccines"; *Nat. Biotechnol.* 15(1):29-34.
Giebel, et al. (1995) "Screening of Cyclic Peptide Phage Libraries Identifies Ligands That Bind Streptavidin with High Affinities"; *Biochemistry* 34(47):15430-15435.
Goldenberg & Creighton (1983) "Circular and Circularly Permuted Forms of Bovine Pancreatic Trypsin Inhibitor"; *J. Mol. Biol.* 165(2):407-413.
Graf & Schachman "Random circular permutation of genes and expressed polypeptide chains: application of the method to the catalytic chains of aspartate transcarbamoylase"; *Proc Natl Acad Sci U S A.* 93(21); Oct. 15, 1996:11591-11596.
Hanes, et al. (1997) "In Vitro Selection and Evolution of Functional Proteins by Using Ribosome Display"; *PNAS USA* 94(10:4937-4942.
Heinemann, et al. (1995) "Circular Permutation of Polypeptide Chains. Implications for Protein Folding and Stability"; *Prog Biophys Mol Biol.* 64:121-143.
Hoogenboom, H.R., "Designing and optimizing library selection strategies for generating high-affinity antibodies"; *Trends in Biotechnology*, vol. 15, Issue 2, Feb. 1997, pp. 62-70.
James, et al. (2003) "Antibody Multispecificity Media Ted by Conformational Diversity"; *Science* 299:1362-1367.
Jung, et al. (1998) "Surface Display of Zymomonas Mobilis Levansucrase by Using the Ice-nucleation Protein of Pseudomonas Syringae"; *Nat Biotechnol.* 16(6):576-580.
Kim, et al. (2000) "Isolation of Peptide Ligands That Inhibit Glutamate Racemase Activity from a Random Phage Display Library"; *J Biomol. Screen.* 5(6):435-440.
Kjaergaard, et al. (2001) "Novel Zn(2+)-Chelating Peptides Selected from a Fimbria-Displayed Random Peptide Library"; *Appl Environ Microbiol.* 67(12):5467-5473.
Kodadek (2001) "Protein Microarrays: Prospects and Problems"; *Chem. Biol.* 8(2):105-115.
Koebnik, et al., "Structural and functional roles of the surface-exposed loops of the beta-barrel membrane protein OmpA from *Escherichia coli*"; *Journal of Bacteriology* vol. 181, No. 12, Jun. 1999, p. 3688-3694.
Koebnik, et al., "Structure and function of bacterial outer membrane proteins:barrels in a nutshell"; Molecular Microbiology 37(2), (2000):239-253.
Koebnik, et. al., "Membrane assembly of circularly permuted variants of the *E. coli* outer membrane protein OmpA"; *J Mol Biol.* 250(5); Jul. 28, 1995:617-626.
Koebnik, "Membrane assembly of the *Escherichia coli* outer membrane protein OmpA: exploring sequence constraints on transmembrane beta-strands"; *J Mol Biol.* 285(4); Jan. 29, 1999:1801-1810.
Konner & Dupont (2004) "Use of Soluble Recombinant Decoy Receptor Vascular Endothelial Growth Factor Trap (VEGF Trap) to Inhibit Vascular Endothelial Growth Factor Activity"; *Clin. Colorectal. Cancer 4 Suppl.* 2:S81-S85.
Ladner, R., :Constrained peptides as binding entities; *Trends in Biotechnology*, vol. 13, Issue 10, Oct. 1995, pp. 426-430.
Lee, et al. (2003) "Microbial Cell-Surface Display"; *Trends in Biotechnology*, 21(1):46-52.
Ley., et al., "Obtaining a family of high-affinity, high-specificity protein inhibitors of plasmin and plasma kallikrein"; *Molecular Diversity*, vol. 2, Nos. 1-2:119-124, (Oct. 1996).
Lowman., et al., "Selecting high-affinity binding proteins by monovalent phage display"; *Biochemistry* 30(45); Nov. 12, 1991:10832-10838.

Lu, et al. (1995) "Expression of Thioredoxin Random Peptide Libraries on the *Escherichia coli* Cell Surface as Functional Fusions to Flagellin: A System Designed for Exploring Protein-Protein Interactions"; *Biotechnology* 13(4):366-372.
Macintyre, et al. (1987) "The signal sequence of an *Escherichia coli* outer membrane protein can mediate translocation of a not normally secreted protein across the plasma membrane"; *J. Biol. Chem.*, vol. 262, Issue 17:8416-8422.
Markland, et al., "Affinity maturation of proteins displayed on surface of M13 bacteriophage as major coat protein fusions"; *Methods in Enzymology*, vol. 267, (1996), pp. 68-82.
Markland, et al., "Iterative Optimization of High-Affinity Protease Inhibitors Using Phage Display. 2 Plasma Kallikrein and Thrombin"; *Biochemistry* 35 (24), 1996; pp. 8058-8067.
Markland, et al., "Iterative Optimization of High-Affinity Protease Inhibitors Using Phage Display. 1. Plasmin"; *Biochemistry*,35 (24),1996, pp. 8045-8057.
Markland, et al., "Selection for protease inhibitors using bacteriophage display"; *Methods in Enzymology* vol. 267, (1996), pp. 28-51.
Matthews & Wells (1993) "Substrate phage: selection of protease substrates by monovalent phage display"; *Science* 260(5111):1113-1117.
Maurer, et al. (1997) "Autodisplay: One-Component System for Efficient Surface Display and Release of Soluble Recombinant Proteins from *Escherichia coli*"; *J. Bacteriol.* 179(3):794-804.
Mejare, et al. (1998) "Selection of cadmium specific hexapeptides and their expression as OmpA fusion proteins in *Escherichia coli*"; *Protein Engineering*, vol. 11: 489-494.
Morimoto, et al. (2004) "Gene Expression Profiling of Human Colon Xenograft Tumors Following Treatment with SU11248, a Multitargeted Tyrosine Kinase Inhibitor"; *Oncogene* 23(8):1618-1626.
Müller, et al. (2003) "Random Peptide Libraries Displayed on Adeno-Associated Virus to Select for Targeted Gene Therapy Vectors"; *Nat Biotechnol.* 21(9):1040-1046.
Nakajima, et al. (2000) "Expression of Random Peptide Fused to Invasin on Bacterial Cell Surface for Selection of Cell Targeting Peptides"; *Gene* 260(1-2):121-131.
Nguyen, et al. (2005) "Evolutionary Optimization of Fluorescent Proteins for Intracellular FRET"; *Nat Biotechnol.* 23(3):355-360.
Olsen, et al. (2003) "High-Throughput Facs Method for Directed Evolution of Substrate Specificity"; *Methods Mol. Biol.* 230:329-342.
Pasqualini & Ruoslahti (1996) "Organ Targeting in Vivo Using Phage Display Peptide Libraries"; *Nature* 380(67572):364-366.
Pautsch & Schulz (2000) "High-Resolution Structure of the OmpA Membrane Domain" *J. Mol. Biol.* 298(2):273-282.
Poul, et al. (2000) "Selection of Tumor Specific Internalizing Human Antibodies from Phage Libraries"; *J Mol Biol.* 301(5):1149-1161.
Proba, et al. (1998) "Antibody scFv Fragments without Disulfide Bonds Made by Molecular Evolution"; *J. Mol. Biol.* 275(2):245-253.
Rice, et al., "Bacterial display using circularly permuted outer membrane protein OmpX yields high affinity peptide ligands"; *Protein Sci.* 15(4); Apr. 2006: 825-836.
Rice, et al., "Directed evolution of a biterminal bacterial display scaffold enhances the display of diverse peptides"; *Protein Eng Des Sel.* 21(7); Jul. 2008:435-442.
Riedel, et al. (2005) "Antiangiogenic Therapy of Head and Neck Squamous Cell Carcinoma by Vascular Endothelial Growth Factor Antisense Therapy"; *Adv. Otorhinolaryngol.* 62:103-120.
Roberts, et al. (1996) "Affinity Maturation of Proteins Displayed on Surface of M13 Bacteriophage as Major Coat Protein Fusions"; Methods Enzymol. 267:68-82.
Shusta, et al. (1999) "Biosynthetic Polypeptide Libraries"; *Curr Opin Biotechnol.* 10(2):117-122.
Smith (1985) "Filamentous Fusion Phage: Novel Expression Vectors That Display Cloned Antigens on the Virion Surface"; *Science* 228(4705):1315-1317.
Ståahl & Uhlén (1997) "Bacterial Surface Display: Trends and Progress"; *Trends Biotechnol.* 15(5):185-192.

(56) References Cited

OTHER PUBLICATIONS

Susman (2005) "Bevacizumab Adds Survival Benefit in Colorectal Cancer"; *Lancet Oncol.* 6:136.
Takahara, et al., "The ompA signal peptide directed secretion of Staphylococcal nuclease A by *Escherichia coli*"; *J. Biol. Chem.*, vol. 260, Issue 5, 2670-2674, (1985).
Taschner, et al. (2002) "Selection of Peptide Entry Motifs by Bacterial Surface Display"; *Biochem. J.*, 367:393-402.
Tuccillo, et al. (2005) "Antitumor Activity of ZD6474, a Vascular Endothelial Growth Factor-2 and Epidermal Growth Factor Receptor Small Molecule Tyrosine Kinase Inhibitor, in Combination with SC-236, A Cyclooxygenase-2 Inhibitor"; *Clin. Cancer Res.* 11(3):1268-1276.
Vogt, et al., "The structure of the outer membrane protein OmpX from *Escherichia coli* reveals possible mechanisms of virulence"; *Structure (London)*, vol. 7, Issue 10, Oct. 1999, pp. 1301-1309.
Wang, et al., "Phage display of proteases and macromolecular inhibitors"; *Methods in Enzymology* vol. 267, (1996), pp. 52-68.
Wentzel, et al. (2001) "Display of Passenger Proteins on the Surface of *Escherichia coli* K-12 by the Enterohemorrhagic *E. coli* Intimin EaeA",*J. Bacteriol.* 183(24):7272-7284.
Whaley, et al. (2000) "Selection of Peptides with Semiconductor Binding Specificity for Directed Nanocrystal Assembly"; *Nature* 405(6787):665-668.
Wild, et al. (2000) "Inhibition of Angiogenesis and Tumor Growth by VEGF121 Toxin Conjugate: Differential Effect on Proliferating Endothelial Cells"; *Br. J. Cancer* 83(8):1077-1083.
Wilson, et al. (2001) "The Use of mRNA Display to Select High-Affinity Protein-Binding Peptides"; *PNAS USA* 98(7):3750-3755.
Wittrup (2001) "Protein Engineering by Cell-Surface Display"; *Curr. Opin. Biotechnol.* 12(4):395-399.
Yang, et al. (1995) "CDR Walking Mutagenesis for the Affinity Maturation of a Potent Human Anti-HIV-1 Antibody into the Picomolar Range"; *J Mol. Biol.* 254(3):392-403.
Yonezawa, et al. (2003) "DNA Display for In Vitro Selection of Diverse Peptide Libraries"; *Nucleic Acids Research* 31:e118.
Yu & Lutz (2011) "Circular Permutation: A Different Way to Engineer Enzyme Structure and Function"; *Trends Biotechnol.* 29(1):18-25.
U.S. Appl. No. 16/005,572, filed Jun. 11, 2018, Daugherty, et al.
Barnes and Sato, "Methods for growth of cultured cells in serum-free medium", Anal. Biochem. (1980) 102(2):255-270.
Boshart et al., "A very strong enhancer is located upstream of an immediate early gene of human cytomegalovirus", Cell (1985) 41(2):521-530.
Casadaban et al., "Analysis of gene control signals by DNA fusion and cloning in *Escherichia coli* ", J. Mol. Biol. (1980) 138(2):179-207.
Chadwick et al., "Safety of a single aerosol administration of escalating doses of the cationic lipid GL-67/DOPE/DMPE-PEG5000 formulation to the lungs of normal volunteers", Gene Therapy (1997) 4(9):937-942.
Chang et al., "Phenotypic expression in *E. coli* of a DNA sequence coding for mouse dihydrofolate reductase", Nature (1978) 275(5681):615-624.
Dalbie-McFarland et al., Oligonucleotide-directed mutagenesis as a general and powerful method for studies of protein function , Proc. Natl. Acad. Sci USA (1982) 79:6409-6413.
Daugherty et al., "Antibody affinity maturation using bacterial surface display", Protein Eng. (1998) 11(9):825-832.
DeBoer et al., "A flow- and time-dependent index of ischemic injury after experimental coronary occlusion and reperfusion", Proc. Natl. Acad. Sci. USA (1983) 80(18):5784-5788.
Deshayes et al., "Rapid identification of small binding motifs with high-throughput phage display: discovery of peptidic antagonists of IGF-1 function", Chem. Biol. (2002) 9(4):495-505.
Dijkema et al., "Cloning and expression of the chromosomal immune interferon gene of the rat", Embo J. (1985) 4(3):761-767.
Edge, "Total synthesis of a human leukocyte interferon gene", Nature (1981) 292:756-762.

Eldridge et al. "An in vitro selection strategy for conferring protease resistance to ligand binding peptides", Prot. Eng. Design Select. (2009) 22(11):691-698.
Fleetwood et al., "Surface display of a single-domain antibody library on Gram-positive bacteria", Cell Mol. Life Sci. (2013) 70(6):1081-1093.
Goddard et al. (1997) "A second dose of a CFTR cDNA-liposome complex is as effective as the first dose in restoring cAMP-dependent chloride secretion to null CF mice trachea", Gene Therapy 4(11): 1231-1236.
Goeddel et al., "Direct expression in *Escherichia coli* of a DNA sequence coding for human growth", Nature (1979) 281 (5732):544-548.
Goeddel et al. (1980) "Synthesis of human fibroblast interferon by *E. coli* ", Nucleic Acids Res.8(18):4057-4074.
Gokhale et al, (1997) "Antisense rat oligodeoxyribonucleotide is protected by liposomal encapsulation and inhibits Raf-1 protein expression in vitro and in vivo: implication for gene therapy of radioresistant cancer", Gene Therapy4(12):1289-1299.
Gorman et al. (1982) "The Rous sarcoma virus long terminal repeat is a strong promoter when introduced into a variety of eukaryotic cells by DNA-mediated transfection", Proc. Natl. Acad Sci. USA 79(22):6777-6781.
Gorman et al. (1997) "Efficient in vivo delivery of DNA to pulmonary cells using the novel lipid EDMPC", Gene Therapy 4(9):983-992.
Griffiths and Tawfik, "Man-made enzymes—from design to in vitro compartmentalization", Curr. Opin. Biotechnol. (2000) 11(4):338-353.
Grussenmeyer et al. (1985) "Complexes of polyoma virus medium T antigen and cellular proteins", Proc. Natl. Acad. Sci. USA 82(23):7952-7954.
Guzman et al. (1995) "Tight regulation, modulation, and high-level expression by vectors containing the arabinose PBAD promoter", J. Bacteriol. 177(14):4121-4130.
Ham et al., "Media and growth requirements", Methods Enzymol. (1979) 58:44-93.
Harvey et al. (2004) "Anchored periplasmic expression, a versatile technology for the isolation of high-affinity antibodies from *Escherichia coli* -expressed libraries", Proc. Natl. Acad. Sci. USA 101(25):9193-9198.
Hopp et al. (1988) "A Short Polypeptide Marker Sequence Useful for Recombinant Protein Identification and Purification", Nature Biotechnol. 6:1204-1210.
Hopp and Woods, (1981) "Prediction of protein antigenic determinants from amino acid sequences", Proc. Natl. Acad. Sci. USA 78(6):3824-3828.
Jabaiah and Daugherty, (2011) "Directed Evolution of Protease Beacons that Enable Sensitive Detection of Endogenous MT1-MMP Activity in Tumor Cell Lines", Chem. & Biol. 18(3):392-401.
Jay et al. (1984) "Chemical synthesis of a biologically active gene for human immune interferon-gamma Prospect for site-specific mutagenesis and structure-function studies", J. Biol. Chem. 259(10):6311-6317.
Johnston et al. (1982) "Isolation of the yeast regulatory gene GAL4 and analysis of its dosage effects on the galactose/melibiose regulon", Proc. Natl. Acad. Sci. USA79(22):6971-6975.
Jose J, and Meyer TF. (2007) "The autodisplay story, from discovery to biotechnical and biomedical applications"; Microbiol Mol Biol Rev. Dec;71(4):600-19.
Kenrick et al., "Flow Cytometric Sorting of Bacterial Surface Displayed Libraries", Curr. Protocol Cytom. (2007) Chapter 4, Unit 4.6 (Published online Oct. 2007, Wiley Interscience).
Kiick et al., (2001) "Identification of an expanded set of translationally active methionine analogues in *Escherichia coli* ", FEBS Lett. 502(1-2):25-30.
Kiick et al., (2002) "Incorporation of azides into recombinant proteins for chemoselective modification by the Staudinger ligation", Proc. Natl. Acad. Sci. USA 99(1):19-24.
Kirshenbaurn et al. (2002) "Biosynthesis of proteins incorporating a versatile set of phenylalanine analogues", Chembiochem. 3(2-3):235-237.

(56) References Cited

OTHER PUBLICATIONS

Kjaergaard et al. (2000) "Sequestration of zinc oxide by fimbrial designer chelators", Appl. Environ. Microbiol. 66(1):10-14.

Kyte and Doolittle (1982) "A simple method for displaying the hydropathic character of a protein", J. Mol. Biol. 157(1):105-132.

Lowman, HB, "Bacteriophage display and discovery of peptide leads for drug development", Ann. Rev. Biophys. Biomol. Struct. (1997) 26:401-424.

McKnight, "Functional relationships between transcriptional control signals of the thymidine kinase gene of herpes simplex virus", Cell (1982) 31(2 Pt 1):355-365.

Nakamura et al. (2002) "Stable "zeta" peptides that act as potent antagonists of the high-affinity IgE receptor", Proc. Natl. Acad. Sci. USA 99(3):1303-1308.

Nambair et al. (1984) "Total synthesis and cloning of a gene coding for the ribonuclease S protein", Science 223:1299-1301.

Nguyen et al., "Improving SH3 domain ligand selectivity using a non-natural scaffold", Chem. Biol.(2000) 7(7):463-473.

Onodera et al. (1998) "Successful peripheral T-lymphocyte-directed gene transfer for a patient with severe combined immune deficiency caused by adenosine deaminase deficiency", Blood 91(1):30-36.

Sharma et al. (2000) "Efficient introduction of aryl bromide functionality into proteins in vivo", Febs Lett. 467(1):37-40.

Shimazu et al. (2001) "Cell surface display of organophosphorus hydrolase using ice nucleation protein", Biotechnol. Prog. 17:76-80.

Siebenlist et al., "*E. coli* RNA polymerase interacts homologously with two different promoters", Cell (1980) 20(2):269-281.

Silver et al. (1984) "Amino terminus of the yeast GAL4 gene product is sufficient for nuclear localization", Proc. Natl. Acad. Sci. USA 81(19):5951-5955.

Simon et al. (1992) "Peptoids: a modular approach to drug discovery", Proc. Natl.Acad. Sci. USA 89(20):9367-9371.

Skerra, A, (2000) "Engineered protein scaffolds for molecular recognition", J. Mol. Recog. 13(4):167-187.

Stemmer et al. (1995) "Single-step assembly of a gene and entire plasmid from large numbers of Oligodeoxyribonucleotides", Gene 64:49-53.

Takeuchi T et al. (2000) "Cellular Location of Membrane-type Serine Protease 1 and Identification of Protease-activated Receptor-2 and Single-chain Urokinase-type Plasminogen Activator as Substrates", J.Biol. Chem. 275(34): 26333-26342.

Tripp et al. (2001) "Investigation of the 'switch-epitope' concept with random peptide libraries displayed as thioredoxin loop fusions", Protein Eng. 14(5):367-377.

van Bloois et al., "Decorating microbes: surface display of proteins on", Trends in Biotech. (2011) 29(2):79-86.

Xu and Lee (1999) "Display of polyhistidine peptides on the *Escherichia coli* cell surface by using outer membrane protein C as an anchoring motif", Appl. Environ. Microbial. 65(11):5142-5147.

\* cited by examiner

SEQUENCE LISTING

```
<160> NUMBER OF SEQ ID NOS: 40

<210> SEQ ID NO 1
<211> LENGTH: 171
<212> TYPE: PRT
<213> ORGANISM: Escherichia coli

<400> SEQUENCE: 1

Met Lys Lys Ile Ala Cys Leu Ser Ala Leu Ala Ala Val Leu Ala Phe
1               5                   10                  15

Thr Ala Gly Thr Ser Val Ala Ala Thr Ser Thr Val Thr Gly Gly Tyr
            20                  25                  30

Ala Gln Ser Asp Ala Gln Gly Gln Met Asn Lys Met Gly Gly Phe Asn
        35                  40                  45

Leu Lys Tyr Arg Tyr Glu Glu Asp Asn Ser Pro Leu Gly Val Ile Gly
    50                  55                  60

Ser Phe Thr Tyr Thr Glu Lys Ser Arg Thr Ala Ser Ser Gly Asp Tyr
65                  70                  75                  80

Asn Lys Asn Gln Tyr Tyr Gly Ile Thr Ala Gly Pro Ala Tyr Arg Ile
                85                  90                  95

Asn Asp Trp Ala Ser Ile Tyr Gly Val Val Gly Val Gly Tyr Gly Lys
            100                 105                 110

Phe Gln Thr Thr Glu Tyr Pro Thr Tyr Lys His Asp Thr Ser Asp Tyr
        115                 120                 125

Gly Phe Ser Tyr Gly Ala Gly Leu Gln Phe Asn Pro Met Glu Asn Val
    130                 135                 140

Ala Leu Asp Phe Ser Tyr Glu Gln Ser Arg Ile Arg Ser Val Asp Val
145                 150                 155                 160

Gly Thr Trp Ile Ala Gly Val Gly Tyr Arg Phe
                165                 170

<210> SEQ ID NO 2
<211> LENGTH: 4
<212> TYPE: PRT
<213> ORGANISM: Artificial
```

```
<220> FEATURE:
<223> OTHER INFORMATION: linker

<400> SEQUENCE: 2

Gly Gly Ser Gly
1

<210> SEQ ID NO 3
<211> LENGTH: 3
<212> TYPE: PRT
<213> ORGANISM: Artificial
<220> FEATURE:
<223> OTHER INFORMATION: linker

<400> SEQUENCE: 3

Gly Arg Lys
1

<210> SEQ ID NO 4
<211> LENGTH: 3
<212> TYPE: PRT
<213> ORGANISM: Artificial
<220> FEATURE:
<223> OTHER INFORMATION: linker

<400> SEQUENCE: 4

Gly Thr Lys
1

<210> SEQ ID NO 5
<211> LENGTH: 3
<212> TYPE: PRT
<213> ORGANISM: Artificial
<220> FEATURE:
<223> OTHER INFORMATION: linker

<400> SEQUENCE: 5

Gly Lys Lys
1

<210> SEQ ID NO 6
<211> LENGTH: 4
<212> TYPE: PRT
<213> ORGANISM: Artificial
<220> FEATURE:
<223> OTHER INFORMATION: linker

<400> SEQUENCE: 6

Gly Ser Lys Arg
1

<210> SEQ ID NO 7
<211> LENGTH: 4
<212> TYPE: PRT
<213> ORGANISM: Artificial
<220> FEATURE:
<223> OTHER INFORMATION: linker

<400> SEQUENCE: 7

Gly Arg Gln Lys
1

<210> SEQ ID NO 8
<211> LENGTH: 4
<212> TYPE: PRT
<213> ORGANISM: Artificial
<220> FEATURE:
```

```
<223> OTHER INFORMATION: linker

<400> SEQUENCE: 8

Ser Trp Pro Asn
1

<210> SEQ ID NO 9
<211> LENGTH: 4
<212> TYPE: PRT
<213> ORGANISM: Artificial
<220> FEATURE:
<223> OTHER INFORMATION: linker

<400> SEQUENCE: 9

Pro Arg Lys Ser
1

<210> SEQ ID NO 10
<211> LENGTH: 5
<212> TYPE: PRT
<213> ORGANISM: Artificial
<220> FEATURE:
<223> OTHER INFORMATION: linker

<400> SEQUENCE: 10

Gly Arg Thr Arg Lys
1               5

<210> SEQ ID NO 11
<211> LENGTH: 5
<212> TYPE: PRT
<213> ORGANISM: Artificial
<220> FEATURE:
<223> OTHER INFORMATION: linker

<400> SEQUENCE: 11

Gly Arg Lys Arg Asn
1               5

<210> SEQ ID NO 12
<211> LENGTH: 5
<212> TYPE: PRT
<213> ORGANISM: Artificial
<220> FEATURE:
<223> OTHER INFORMATION: linker

<400> SEQUENCE: 12

Gly Ala Thr Arg Arg
1               5

<210> SEQ ID NO 13
<211> LENGTH: 5
<212> TYPE: PRT
<213> ORGANISM: Artificial
<220> FEATURE:
<223> OTHER INFORMATION: linker

<400> SEQUENCE: 13

Gly Ser Gln Ser Lys
1               5

<210> SEQ ID NO 14
<211> LENGTH: 6
<212> TYPE: PRT
<213> ORGANISM: Artificial
<220> FEATURE:
<223> OTHER INFORMATION: linker
```

```
<400> SEQUENCE: 14

Gly Thr Lys Arg Tyr His
1               5

<210> SEQ ID NO 15
<211> LENGTH: 6
<212> TYPE: PRT
<213> ORGANISM: Artificial
<220> FEATURE:
<223> OTHER INFORMATION: linker

<400> SEQUENCE: 15

Gly Arg Arg His Tyr Lys
1               5

<210> SEQ ID NO 16
<211> LENGTH: 6
<212> TYPE: PRT
<213> ORGANISM: Artificial
<220> FEATURE:
<223> OTHER INFORMATION: linker

<400> SEQUENCE: 16

Gly Asn Arg Arg His Arg
1               5

<210> SEQ ID NO 17
<211> LENGTH: 6
<212> TYPE: PRT
<213> ORGANISM: Artificial
<220> FEATURE:
<223> OTHER INFORMATION: linker

<400> SEQUENCE: 17

Gly Ser Lys Gln Ser Lys
1               5

<210> SEQ ID NO 18
<211> LENGTH: 6
<212> TYPE: PRT
<213> ORGANISM: Artificial
<220> FEATURE:
<223> OTHER INFORMATION: linker

<400> SEQUENCE: 18

Gly Ser Lys Ser Arg Arg
1               5

<210> SEQ ID NO 19
<211> LENGTH: 6
<212> TYPE: PRT
<213> ORGANISM: Artificial
<220> FEATURE:
<223> OTHER INFORMATION: linker

<400> SEQUENCE: 19

Gly Arg Lys Asn Ser His
1               5

<210> SEQ ID NO 20
<211> LENGTH: 6
<212> TYPE: PRT
<213> ORGANISM: Artificial
<220> FEATURE:
<223> OTHER INFORMATION: linker
```

```
<400> SEQUENCE: 20

Gly Thr Arg Gly Ser Gln
1               5

<210> SEQ ID NO 21
<211> LENGTH: 6
<212> TYPE: PRT
<213> ORGANISM: Artificial
<220> FEATURE:
<223> OTHER INFORMATION: linker

<400> SEQUENCE: 21

Gly His Arg Ser His Arg
1               5

<210> SEQ ID NO 22
<211> LENGTH: 6
<212> TYPE: PRT
<213> ORGANISM: Artificial
<220> FEATURE:
<223> OTHER INFORMATION: linker

<400> SEQUENCE: 22

Gly Asp Arg Lys Arg Arg
1               5

<210> SEQ ID NO 23
<211> LENGTH: 6
<212> TYPE: PRT
<213> ORGANISM: Artificial
<220> FEATURE:
<223> OTHER INFORMATION: linker

<400> SEQUENCE: 23

Gly Ala Arg Gly Arg His
1               5

<210> SEQ ID NO 24
<211> LENGTH: 6
<212> TYPE: PRT
<213> ORGANISM: Artificial
<220> FEATURE:
<223> OTHER INFORMATION: linker

<400> SEQUENCE: 24

Gly Thr His Asn Ser Gln
1               5

<210> SEQ ID NO 25
<211> LENGTH: 6
<212> TYPE: PRT
<213> ORGANISM: Artificial
<220> FEATURE:
<223> OTHER INFORMATION: linker

<400> SEQUENCE: 25

Gly Pro Asn Lys Ser Arg
1               5

<210> SEQ ID NO 26
<211> LENGTH: 6
<212> TYPE: PRT
<213> ORGANISM: Artificial
<220> FEATURE:
<223> OTHER INFORMATION: linker

<400> SEQUENCE: 26
```

```
Gly Pro His Asn Ser Arg
1               5

<210> SEQ ID NO 27
<211> LENGTH: 8
<212> TYPE: PRT
<213> ORGANISM: Artificial
<220> FEATURE:
<223> OTHER INFORMATION: linker

<400> SEQUENCE: 27

His Arg Gly Tyr His Ala Gln Arg
1               5

<210> SEQ ID NO 28
<211> LENGTH: 6
<212> TYPE: PRT
<213> ORGANISM: Artificial
<220> FEATURE:
<223> OTHER INFORMATION: linker

<400> SEQUENCE: 28

Gly Gly Gln Ser Gly Gln
1               5

<210> SEQ ID NO 29
<211> LENGTH: 15
<212> TYPE: PRT
<213> ORGANISM: Artificial
<220> FEATURE:
<223> OTHER INFORMATION: CRP-binding peptide

<400> SEQUENCE: 29

Glu Trp Ala Cys Asn Asp Arg Gly Phe Asn Cys Gln Leu Gln Arg
1               5                   10                  15

<210> SEQ ID NO 30
<211> LENGTH: 19
<212> TYPE: PRT
<213> ORGANISM: Artificial
<220> FEATURE:
<223> OTHER INFORMATION: VEGF-binding peptide

<400> SEQUENCE: 30

Val Glu Pro Asn Cys Asp Ile His Val Met Trp Glu Trp Glu Cys Phe
1               5                   10                  15

Glu Arg Leu

<210> SEQ ID NO 31
<211> LENGTH: 33
<212> TYPE: PRT
<213> ORGANISM: Artificial
<220> FEATURE:
<223> OTHER INFORMATION: mini Z domain

<400> SEQUENCE: 31

Phe Asn Met Gln Gln Gln Arg Arg Phe Tyr Glu Ala Leu His Asp Pro
1               5                   10                  15

Asn Leu Asn Glu Glu Gln Arg Asn Ala Lys Ile Lys Ser Ile Arg Asp
            20                  25                  30

Asp

<210> SEQ ID NO 32
<211> LENGTH: 11
```

```
<212> TYPE: PRT
<213> ORGANISM: Artificial
<220> FEATURE:
<223> OTHER INFORMATION: T7 tag

<400> SEQUENCE: 32

Met Ala Ser Met Thr Gly Gly Gln Gln Met Gly
1               5                   10

<210> SEQ ID NO 33
<211> LENGTH: 13
<212> TYPE: PRT
<213> ORGANISM: Artificial
<220> FEATURE:
<223> OTHER INFORMATION: P2 peptide

<400> SEQUENCE: 33

Pro Ala Pro Ser Ile Asp Arg Ser Thr Lys Pro Pro Leu
1               5                   10

<210> SEQ ID NO 34
<211> LENGTH: 20
<212> TYPE: PRT
<213> ORGANISM: Artificial
<220> FEATURE:
<223> OTHER INFORMATION: extended linker

<400> SEQUENCE: 34

Gly Gly Gly Ser Gly Gly Gly Ser Gly Gly Gly Ser Gly Gly Gly Ser
1               5                   10                  15

Gly Gly Gly Ser
            20

<210> SEQ ID NO 35
<211> LENGTH: 5
<212> TYPE: PRT
<213> ORGANISM: Artificial
<220> FEATURE:
<223> OTHER INFORMATION: CPX sequence containing SfiI restriction site

<400> SEQUENCE: 35

Gly Gln Ser Gly Gln
1               5

<210> SEQ ID NO 36
<211> LENGTH: 15
<212> TYPE: PRT
<213> ORGANISM: Artificial
<220> FEATURE:
<223> OTHER INFORMATION: streptavidin binding peptide

<400> SEQUENCE: 36

Ala Glu Cys His Pro Gln Gly Pro Pro Cys Ile Glu Gly Arg Lys
1               5                   10                  15

<210> SEQ ID NO 37
<211> LENGTH: 4
<212> TYPE: PRT
<213> ORGANISM: Artificial Sequence
<220> FEATURE:
<223> OTHER INFORMATION: Linker

<400> SEQUENCE: 37

Gly Gly Gly Ser
1
```

```
<210> SEQ ID NO 38
<211> LENGTH: 16
<212> TYPE: PRT
<213> ORGANISM: Artificial Sequence
<220> FEATURE:
<223> OTHER INFORMATION: Linker

<400> SEQUENCE: 38

Gly Gly Gly Ser Gly Gly Gly Ser Gly Gly Gly Ser Gly Gly Gly Ser
1               5                   10                  15

<210> SEQ ID NO 39
<211> LENGTH: 24
<212> TYPE: PRT
<213> ORGANISM: Artificial Sequence
<220> FEATURE:
<223> OTHER INFORMATION: Linker

<400> SEQUENCE: 39

Gly Gly Gly Ser Gly Gly Gly Ser Gly Gly Gly Ser Gly Gly Gly Ser
1               5                   10                  15

Gly Gly Gly Ser Gly Gly Gly Ser
            20

<210> SEQ ID NO 40
<211> LENGTH: 6
<212> TYPE: PRT
<213> ORGANISM: Artificial sequence
<220> FEATURE:
<223> OTHER INFORMATION: synthetic sequence

<400> SEQUENCE: 40

Arg Lys Ser His Gln Asn
1               5
```

METHODS FOR ENHANCING BACTERIAL CELL DISPLAY OF PROTEINS AND PEPTIDES

CROSS-REFERENCE TO RELATED APPLICATIONS

This application is a continuation of U.S. patent application Ser. No. 14/717,679, filed May 20, 2015, now U.S. Pat. No. 9,695,415, which application is a continuation of U.S. patent application Ser. No. 13/615,072, filed Sep. 13, 2012, now U.S. Pat. No. 9,062,107, which application is a continuation of U.S. patent application Ser. No. 12/220,448, filed Jul. 24, 2008, now U.S. Pat. No. 8,293,685, which application claims the benefit of U.S. Provisional Application No. 60/962,086, filed Jul. 26, 2007, which applications are incorporated by reference herein in their-entireties.

STATEMENT REGARDING FEDERALLY SPONSORED RESEARCH OR DEVELOPMENT

This invention was made with government support under U.S. Army Contract DAAD-19-03-D-0004 awarded by the Institute for Collaborative Biotechnologies. The government has certain rights in the invention.

TECHNICAL FIELD

The invention is in the field of protein engineering. In particular, the disclosure relates generally to methods of making and using bacterial display polypeptide libraries, including methods for enhancing the display of proteins and peptides at the surface of bacteria by using vectors encoding circularly permuted OmpX (CPX) variants containing optimized linkers and selected mutations at positions 165 and 166.

BACKGROUND

Display methodologies have proven invaluable for the discovery, production, and optimization of proteins and peptides in a variety of biotechnological applications. Various approaches including phage display (Smith, G. P. (1985) *Science*, 228, 1315-1317), mRNA (Wilson et al. (2001) *Proc. Natl. Acad. Sci. USA*, 98, 3750-3755) and DNA display (Yonezawa et al. (2003) *Nucleic Acids Res.*, 31, e118), ribosome display (Hanes, J. & Pluckthun, A. (1997) *Proc. Natl. Acad. Sci. USA*, 94, 4937-42), eukaryotic virus display (Bupp, K. & Roth, M. J. (2002) *Mol. Ther.*, 5, 329-335; Muller et al. (2003) *Nat. Biotechnol.*, 21:1040-1046), yeast display (Boder, E. T. & Wittrup, K. D. (1997) *Nat. Biotechnol.*, 15, 553-557), and bacterial display (Lu et al. (1995) *Biotechnology* (N Y), 13, 366-372) have been developed to screen diverse molecular repertoires for desired activities. In particular, bacterial display libraries have enabled antibody affinity maturation (Daugherty et al. (2000) *Proc. Natl. Acad. Sci. USA*, 97, 2029-2034), the discovery of protein binding peptides (Bessette et al. (2004) *Protein Eng. Des. Sel.*, 17, 731-739), cell-specific ligands (Dane et al. (2006) *J. Immunol. Methods*, 309, 120-129; Nakajima et al. (2000) *Gene*, 260, 121-131), and the identification of optimal protease substrates (Boulware, K. T. & Daugherty, P. S. (2006) *Proc. Natl. Acad. Sci. USA*, 103, 7583-7588). One of the key advantages of bacterial surface display is the ability to use flow cytometry for quantitative screening of the libraries, allowing for real-time analysis of binding affinity and specificity to optimize the screening process (Wittrup, K. D. (2001) *Curr. Opin. Biotechnol.*, 12, 395-399). Additionally, the ease of genetic manipulation, high transformation efficiency, and rapid growth rate make *E. coli* a well-suited host for display. A broad range of bacterial surface display systems have been developed allowing for insertional or terminally fused peptides and proteins to be displayed on the cell surface. Several outer membrane proteins and cellular appendage proteins have been used to present polypeptides as insertional fusions (Bessette et al. (2004) *Protein Eng. Des. Sel.*, 17, 731-739; Charbit et al. (1986) *Embo J.*, 5, 3029-3037; Taschner et al. (2002) *Biochem. 1*, 367, 393-402). The ice nucleation protein (Jung et al. (1998) *Nat. Biotechnol.*, 16, 576-580), intimins (Christmann et al. (1999) *Protein Eng.*, 12, 797-806), and LppOmpA (Francisco et al. (1992) *Proc. Natl. Acad. Sci. USA*, 89, 2713-2717) have been used to display proteins on the C-terminus of a transmembrane scaffold while N-terminal display has been accomplished using auto-transporters IgA1 protease and EstA (Maurer et al. (1997) *J Bacteriol*, 179, 794-804).

Recently, a unique bacterial display scaffold was developed that allows for N- and/or C-terminal display from a circularly permuted variant of outer membrane protein OmpX (CPX) (Rice et al. (2006) *Protein Sci.*, 15, 825-836). This scaffold enables display of peptides on both termini, but with reduced efficiency when compared to that obtained using insertions into OmpX. Reduced membrane localization of CPX may result from slower folding rates and reduced stability that has been described previously for circularly permuted proteins (Heinemann, U. & Hahn, M. (1995) *Prog. Biophys. Mol. Biol.*, 64, 121-143). Regardless, reduced display efficiency requires longer induction times to achieve sufficient display for screening by FACS. Importantly, inefficient display can create an undesired selection pressure resulting in growth biases, reduced viability, or differing levels of passenger localization on the cell surface. As a result, screening based upon cell fluorescence can favor passengers most efficiently localized to the surface, rather than passengers enhanced for the properties of interest (e.g., binding affinity).

Thus, there remains a need for additional vectors for bacterial cell display and methods that would more effectively display proteins and peptides.

SUMMARY

The present invention relates to bacterial cell display and methods for enhancing the display of proteins and peptides at the surface of bacteria by using vectors encoding circularly permuted OmpX (CPX) variants containing optimized linkers and selected mutations at positions 165 and 166.

In one aspect, the invention includes a circularly permuted OmpX (CPX) variant comprising a linker joining the native N-terminus and C-terminus, wherein the linker is 3-8 residues in length and comprises a glycine and one or more basic amino acids. In one embodiment, the first residue of the linker is a glycine. In certain embodiments, the linker comprises at least two basic residues, for example, at least two arginine residues or two lysine residues, or at least one arginine residue and at least one lysine residue. In one embodiment the linker is 5 residues in length. In another embodiment, the linker is 6 residues in length. In certain embodiments, the first residue of the linker is a glycine and the third and sixth residues of the linker are selected from the group consisting of arginine, lysine, serine, histidine, glutamine, and asparagine. In certain embodiments, the linker comprises a sequence selected from the group consisting of SEQ ID NOS:2-27.

The CPX variant of any of the above embodiments may further comprise one or more mutations that increase the display efficiency of a passenger peptide carried by the CPX variant. In certain embodiments, a hydrophobic residue is substituted at the position corresponding to A165 of the native OmpX protein (numbered relative to the reference sequence of SEQ ID NO:1). Exemplary mutations include, but are not limited to, A165V, A165L, A165I, A165F. In other embodiments, the amino acid at the position corresponding to G166 (numbered relative to the reference sequence of SEQ ID NO:1) of the native OmpX protein is replaced. Exemplary mutations include, but are not limited to, G166S and G166A.

In certain embodiments, the CPX variant of any of the above embodiments, further comprises a passenger polypeptide, which can be fused to either the N-terminus or the C-terminus of the CPX variant. In certain embodiments, two passenger polypeptides are carried simultaneously by the CPX variant, wherein a first passenger polypeptide is fused to the N-terminus and a second passenger polypeptide is fused to the C-terminus of the CPX variant. A passenger polypeptide can be connected to the N- or C-terminus of a CPX variant by a linker sequence, for example, a linker comprising a sequence selected from the group consisting of SEQ ID NO:28 and SEQ ID NO:34 can be used in the practice of the invention.

In certain embodiments, the CPX variant of the invention carries a passenger polypeptide comprising a detectable label. In one embodiment, the passenger polypeptide is a streptavidin binding peptide that binds to streptavidin conjugated to a fluorophore. An exemplary streptavidin binding peptide comprises the amino acid sequence of SEQ ID NO:36. In certain embodiments, two passenger polypeptides are fused to the CPX variant at the N-terminus and C-terminus, respectively, wherein both passenger polypeptides comprise detectable labels, which may be the same or different.

In another aspect, the invention includes a polynucleotide encoding any of the CPX variants described herein.

In another aspect, the invention includes an expression vector comprising a polynucleotide of the invention operably linked to a promoter, wherein the expressed CPX variant is capable of displaying one or more passenger polypeptides on an outer surface of a bacterial cell.

In another aspect, the invention includes a bacterial cell comprising an expression vector of the invention. Exemplary bacterial cells that can be used in the practice of the invention include, but are not limited to, *Escherichia coli, Shigella sonnei, Shigella dysenteriae, Shingella flexneri, Salmonella typhimurium, Salmonella enterica, Enterobacter aerogenes, Serratia marcescens, Yersinia pestis,* and *Klebsiella pneumoniae*.

In another aspect, the invention includes a polypeptide display library comprising a polypeptide displayed by a CPX variant of the invention.

In another aspect, the invention includes a method of making a polypeptide display library, the method comprising:
providing a plurality of expression vectors expressing CPX variants carrying a plurality of passenger polypeptides, transfecting bacterial cells with the expression vectors, and
culturing the bacterial cells under conditions that permit expression of the passenger polypeptides on the surface of the bacterial cells.

In another aspect, the invention includes a method of screening for a CPX variant that displays a passenger polypeptide with greater efficiency in bacteria than another carrier protein carrying the same passenger polypeptide, the method comprising:
transfecting a bacterial cell with an expression vector expressing a CPX variant carrying the passenger polypeptide,
screening for display of the passenger polypeptide at the surface of the bacterial cell within 25 minutes after inducing the expression of the CPX variant carrying the passenger polypeptide; and
comparing the display efficiency of the CPX variant carrying the passenger polypeptide to the display efficiency of another carrier protein carrying the same passenger polypeptide expressed under the same conditions.

The display efficiency of a passenger polypeptide can be increased by screening different CPX variants by this method. For example, a plurality of CPX variants carrying the same passenger polypeptide are screened, wherein each CPX variant comprises a different linker joining the native N-terminus and C-terminus, wherein the linker is 3-8 residues in length and comprises a glycine and one or more basic amino acids, and optionally, a mutation at a position corresponding to A165 or G166 of the native OmpX protein (numbered relative to the reference sequence of SEQ ID NO:1). The CPX variant is selected that displays the passenger polypeptide with the greatest efficiency compared to the plurality of other CPX variants.

In another aspect, the invention provides a method of screening a library of polypeptides for biological activity in the presence of a target molecule, the method comprising: a) providing a polypeptide display library comprising CPX variants carrying a plurality of passenger polypeptides displayed on bacterial cells, b) contacting the plurality of passenger polypeptides with the target molecule, c) assaying for biological activity in the presence of the target molecule, and d) identifying at least one displayed passenger polypeptide that has biological activity. For this purpose, any CPX variant described herein can be used in the polypeptide display library for screening polypeptides. The polypeptide display library can include passenger polypeptides fused to the N- or C- or both terminii of the CPX variants. The biological activity assayed can be enzymatic activity, substrate activity, ligand-binding activity, transport activity, agonist activity, antagonist activity, or any other biological activity. Any target molecule can be chosen, including but not limited to, a receptor, a ligand, an antibody, an antigen, an enzyme, a transporter, a substrate, an inhibitor, an activator, a cofactor, a drug, a nucleic acid, a lipid, a carbohydrate, a glycoprotein, a small organic molecule, or an inorganic molecule.

In one embodiment, the invention includes a method of screening a library of polypeptides for the ability to bind to a target molecule, the method comprising: a) providing a polypeptide display library comprising CPX variants carrying a plurality of passenger polypeptides displayed on bacterial cells, b) contacting the plurality of passenger polypeptides with the target molecule, and c) identifying at least one displayed passenger polypeptide that binds to the target molecule. In one embodiment, the target molecule comprises a detectable label that enables binding of the target molecule to a passenger polypeptide to be determined by detecting the label attached to the target molecule.

Thus, the subject invention is represented by, but not limited to, the following numbered embodiments:

1. A circularly permuted OmpX (CPX) variant comprising a linker joining the native N-terminus and C-terminus, wherein the linker is 3-8 residues in length and comprises a glycine and one or more basic amino acids.
2. The CPX variant of embodiment 1, wherein the first residue of the linker is a glycine.
3. The CPX variant of embodiment 1 or 2, wherein the linker comprises at least two basic residues.
4. The CPX variant of any of embodiments 1-3, wherein the linker comprises two arginine residues.
5. The CPX variant of any of embodiments 1-4, wherein the linker comprises two lysine residues.
6. The CPX variant of any of embodiments 1-5, wherein the linker comprises at least one arginine residue and at least one lysine residue.
7. The CPX variant of any of embodiments 1 to 6, wherein the linker is 5 residues in length.
8. The CPX variant of any of embodiments 1 to 6, wherein the linker is 6 residues in length.
9. The CPX variant of embodiment 8, wherein the first residue of the linker is a glycine and the third and sixth residues of the linker are selected from the group consisting of arginine, lysine, serine, histidine, glutamine, and asparagine.
10. The CPX variant of any of embodiments 1 to 9, wherein the linker comprises a sequence selected from the group consisting of SEQ ID NOS:2-27.
11. The CPX variant of any of embodiments 1 to 10, further comprising one or more mutations that increase the display efficiency of a passenger peptide compared to the CPX variant in the absence of the mutations, wherein at least one mutation is at a position corresponding to A165 or G166 of the native OmpX protein numbered relative to the reference sequence of SEQ ID NO:1.
12. The CPX variant of embodiment 11 comprising an A165V mutation.
13. The CPX variant of embodiment 11 comprising an A165L mutation.
14. The CPX variant of embodiment 11 comprising an A165I mutation.
15. The CPX variant of embodiment 11 comprising an A165F mutation.
16. The CPX variant of any of embodiments 11 to 15 comprising a G166S mutation.
17. The CPX variant of any of embodiments 11 to 15 comprising a G166A mutation.
18. The CPX variant of any of embodiments 1 to 17, further comprising a passenger polypeptide fused to the N-terminus.
19. The CPX variant of embodiment 18, further comprising a linker between the N-terminus and the passenger polypeptide, wherein said linker comprises a sequence selected from the group consisting of SEQ ID NO:28 and SEQ ID NO:34.
20. The CPX variant of any of embodiments 1 to 17, further comprising a passenger polypeptide fused to the C-terminus.
21. The CPX variant of embodiment 20, further comprising a linker between the C-terminus and the passenger polypeptide, wherein said linker comprises a sequence selected from the group consisting of SEQ ID NO:28 and SEQ ID NO:34.
22. The CPX variant of any of embodiments 1 to 21, further comprising a first passenger polypeptide fused to the N-terminus and a second passenger polypeptide fused to the C-terminus.
23. The CPX variant of embodiment 22, wherein the first passenger polypeptide or the second passenger polypeptide further comprises a detectable label.
24. The CPX variant of embodiment 23, wherein the first passenger polypeptide or the second passenger polypeptide comprises a streptavidin binding peptide.
25. The CPX variant of embodiment 24, wherein the detectable label is streptavidin conjugated to a fluorophore.
26. The CPX variant of embodiment 24, wherein the streptavidin binding peptide comprises the sequence of SEQ ID NO:36.
27. The CPX variant of embodiment 23, wherein both the first passenger polypeptide and the second passenger polypeptide comprise detectable labels.
28. The CPX variant of embodiment 27, wherein the first passenger polypeptide comprises a different detectable label than the second passenger polypeptide.
29. The CPX variant of any of embodiments 22 to 28, further comprising a linker between the first passenger polypeptide and the N-terminus or the second passenger polypeptide and the C-terminus.
30. The CPX variant of embodiment 29, wherein the linker comprises a sequence selected from the group consisting of SEQ ID NO:28 and SEQ ID NO:34.
31. A polynucleotide encoding the CPX variant of any of embodiments 1 to 30.
32. An expression vector comprising the polynucleotide of embodiment 31 operably linked to a promoter, wherein the expressed CPX variant displays one or more passenger polypeptides on an outer surface of a bacterial cell.
33. A bacterial cell comprising the expression vector of embodiment 32.
34. The bacterial cell of embodiment 33, where the bacterial cell is *Escherichia coli, Shigella sonnei, Shigella dysenteriae, Shingella flexneri, Salmonella typhimurium, Salmonella enterica, Enterobacter aerogenes, Serratia marcescens, Yersinia pestis,* or *Klebsiella pneumoniae.*
35. A polypeptide display library comprising a polypeptide displayed by the CPX variant of any of embodiments 1 to 30.
36. A method of making the polypeptide display library of embodiment 35, the method comprising:
   providing a plurality of expression vectors expressing CPX variants carrying a plurality of passenger polypeptides,
   transfecting bacterial cells with said expression vectors, and
   culturing the bacterial cells under conditions that permit expression of said passenger polypeptides on the surface of the bacterial cells.
37. A method of screening for a CPX variant that displays a passenger polypeptide with greater efficiency than another carrier protein carrying the same passenger polypeptide, the method comprising:
   transfecting a bacterial cell with an expression vector expressing a CPX variant carrying the passenger polypeptide,
   screening for display of the passenger polypeptide at the surface of the bacterial cell within 25 minutes after inducing the expression of the CPX variant carrying the passenger polypeptide; and
   comparing the display efficiency of the CPX variant carrying the passenger polypeptide to the display efficiency of another carrier protein carrying the same passenger polypeptide expressed under the same conditions.

38. A method of enhancing the display efficiency of a passenger polypeptide, the method comprising:
   screening a plurality of different CPX variants carrying the same passenger polypeptide according to the method of embodiment 37, wherein each CPX variant comprises a different linker joining the native N-terminus and C-terminus, wherein the linker is 3-8 residues in length and comprises a glycine and one or more basic amino acids, and optionally, a mutation at a position corresponding to A165 or G166 of the native OmpX protein; and
   selecting the CPX variant that displays the passenger polypeptide with the greatest efficiency compared to the plurality of other CPX variants.

39. The method of embodiment 38, wherein the first residue of the linker is a glycine and the third residue of the linker is selected from the group consisting of arginine, lysine, serine, histidine, glutamine, and asparagine.

40. The method of embodiment 39, wherein the linker is 6 residues in length.

41. The method of embodiment 40, wherein the sixth residue of the linker is selected from the group consisting of arginine, lysine, serine, histidine, glutamine, and asparagine.

42. A method of screening a library of polypeptides for the ability to bind to a target molecule, the method comprising:
   a) providing a polypeptide display library comprising CPX variants carrying a plurality of passenger polypeptides displayed on bacterial cells,
   b) contacting the plurality of passenger polypeptides with the target molecule, and
   c) identifying at least one displayed passenger polypeptide that binds to the target molecule.

43. The method of embodiment 42, wherein the target molecule is selected from the group consisting of a receptor, a ligand, an antibody, an antigen, an enzyme, a transporter, a substrate, an inhibitor, an activator, a cofactor, a drug, a nucleic acid, a lipid, a carbohydrate, a glycoprotein, a small organic molecule, and an inorganic molecule.

44. The method of embodiment 42, wherein said target molecule comprises a detectable label, wherein identifying the target molecule bound to at least one passenger polypeptide comprises detecting the label attached to said target molecule.

45. A method of screening a library of polypeptides for biological activity in the presence of a target molecule, the method comprising:
   a) providing a polypeptide display library comprising CPX variants carrying a plurality of passenger polypeptides displayed on bacterial cells,
   b) contacting the plurality of passenger polypeptides with the target molecule,
   c) assaying for biological activity in the presence of the target molecule, and
   d) identifying at least one displayed passenger polypeptide that has biological activity.

46. The method of embodiment 45, wherein the biological activity is enzymatic activity, substrate activity, ligand-binding activity, transport activity, agonist activity, or antagonist activity.

47. The method of embodiment 45, wherein the target molecule is selected from the group consisting of a receptor, a ligand, an antibody, an antigen, an enzyme, a transporter, a substrate, an inhibitor, an activator, a cofactor, a drug, a nucleic acid, a lipid, a carbohydrate, a glycoprotein, a small organic molecule, and an inorganic molecule.

These and other embodiments of the subject invention will readily occur to those of skill in the art in view of the disclosure herein.

DETAILED DESCRIPTION

Figure 1A:
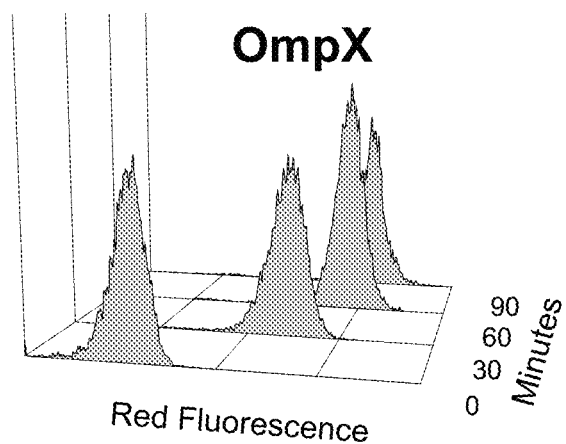
FIGS. 1A to 1C, are plots depicting the bacterial display of a streptavidin (SA)-binding peptide with OmpX (FIG. 1A), CPX (FIG. 1B), and eCPX (FIG. 1C). The SA-binding peptide (AECHPQGPPCIEGRK (SEQ ID NO:36), described by Giebel et al. (1995) *Biochemistry*, 34, 15430-15435) was displayed in *E. coli* as an insertion in OmpX, an N-terminal fusion in CPX, or as an N-terminal fusion in eCPX. Cells were induced at room temperature for time increments between 0 and 90 minutes, then labeled with 100 nM SA-PE, and analyzed by flow cytometry after varying durations of induction.

The practice of the present invention will employ, unless otherwise indicated, conventional methods of pharmacology, chemistry, biochemistry, recombinant DNA techniques and immunology, within the skill of the art. Such techniques are explained fully in the literature. See, e.g., *Handbook of Experimental Immunology*, Vols. I-IV (D. M. Weir and C. C. Blackwell eds., Blackwell Scientific Publications); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.).

All publications, patents and patent applications cited herein, whether supra or infra, are hereby incorporated by reference in their entireties.

I. DEFINITIONS

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a peptide" includes a mixture of two or more such peptides, and the like.

The term "CPX" as used herein refers to a circularly permuted variant of a bacterial outer membrane protein OmpX (see U.S. patent application Ser. No. 10/920,244, which is herein incorporated by reference in its entirety). The CPX protein consists of the native OmpX signal sequence, which is cleaved after translocation; a sequence with an embedded SfiI restriction site (GQSGQ) (SEQ ID NO:35) after which peptides may be inserted; a flexible linking sequence (GGQSGQ) (SEQ ID NO:28); amino acids S54-F148 of the mature OmpX; a GGSG (SEQ ID NO:2) linker joining the native C- and N-termini of OmpX; and amino acids A1-S53 of the mature OmpX. CPX can be used as a protein scaffold for bacterial display of peptides and proteins at the surface of a bacterial cell. An advantage of using CPX in bacterial display is that both its N- and C-termini are exterior to the cell, which allows polypeptides to be displayed from either terminus or from both termini simultaneously. The term CPX includes circularly permuted variants of OmpX from any strain of bacteria, such as *Escherichia coli, Shigella sonnei, Shigella dysenteriae, Shingella flexneri, Salmonella typhimurium, Salmonella enterica, Enterobacter aerogenes, Serratia marcescens, Yersinia pestis*, or *Klebsiella pneumoniae*. The GenBank database contains complete sequences for OmpX proteins from a variety of bacterial isolates, which could be used to produce CPX proteins of the invention. Furthermore, for purposes of the present invention, the term "CPX" refers to a protein which includes modifications, such as deletions, additions and substitutions, for example, replacement of the linker joining the native N- and C-termini of OmpX, substitutions at positions 165 and 166 (numbered with reference to the sequence of native OmpX from *Escherichia coli*, SEQ ID NO:1), incorporation of alternate restriction sites after which polypeptides or peptides may be inserted, or the addition of linkers between the N-terminus or C-terminus of CPX and a passenger polypeptide, so long as the protein maintains biological activity (i.e., ability to efficiently display polypeptides). These modifications may be deliberate, as through site-directed mutagenesis, or may be accidental, such as through mutations of hosts which produce the proteins or errors due to PCR amplification.

The terms "polypeptide", "peptide", "protein", and "amino acid sequence" as used herein generally refer to any compound comprising naturally occurring or synthetic amino acid polymers or amino acid-like molecules including but not limited to compounds comprising amino and/or imino molecules. No particular size is implied by use of the term "peptide", "oligopeptide", "polypeptide", or "protein" and these terms are used interchangeably. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring (e.g., synthetic). Thus, synthetic oligopeptides, dimers, multimers (e.g., tandem repeats, multiple antigenic peptide (MAP) forms, linearly-linked peptides), cyclized, branched molecules and the like, are included within the definition. The terms also include molecules comprising one or more peptoids (e.g., N-substituted glycine residues) and other synthetic amino acids or peptides. (See, e.g., U.S. Pat. Nos. 5,831,005; 5,877,278; and U.S. Pat. No. 5,977,301; Nguyen et al. (2000) *Chem Biol.* 7(7):463-473; and Simon et al. (1992) *Proc. Natl. Acad. Sci. USA* 89(20):9367-9371 for descriptions of peptoids). Non-limiting lengths of peptides suitable for use in the present invention includes peptides of 3 to 5 residues in length, 6 to 10 residues in length (or any integer therebetween), 11 to 20 residues in length (or any integer therebetween), 21 to 75 residues in length (or any integer therebetween), 75 to 100 (or any integer therebetween), or polypeptides of greater than 100 residues in length. Typically, polypeptides useful in this invention can have a maximum length suitable for the intended application. Preferably, the polypeptide is between about 3 and 100 residues in length. Generally, one skilled in art can easily select the maximum length in view of the teachings herein. Further, peptides as described herein, for example synthetic peptides, may include additional molecules such as labels or other chemical moieties (e.g., streptavidin conjugated to phycoerythrin, Alexa dye conjugated to anti-T7 tag). Such moieties may further enhance interaction of the peptides with a ligand and/or further detection of polypeptide display.

Thus, reference to peptides also includes derivatives of the amino acid sequences of the invention including one or more non-naturally occurring amino acid. A first polypeptide is "derived from" a second polypeptide if it is (i) encoded by a first polynucleotide derived from a second polynucleotide encoding the second polypeptide, or (ii) displays sequence identity to the second polypeptide as described herein. Sequence (or percent) identity can be determined as described below. Preferably, derivatives exhibit at least about 50% percent identity, more preferably at least about 80%, and even more preferably between about 85% and 99% (or any value therebetween) to the sequence from which they were derived. Such derivatives can include postexpression modifications of the polypeptide, for example, glycosylation, acetylation, phosphorylation, and the like.

Amino acid derivatives can also include modifications to the native sequence, such as deletions, additions and substitutions (generally conservative in nature), so long as the polypeptide maintains the desired activity. These modifications may be deliberate, as through site-directed mutagenesis, or may be accidental, such as through mutations of hosts that produce the proteins or errors due to PCR amplification. Furthermore, modifications may be made that have one or more of the following effects: increasing efficiency of bacterial display, level of expression, or stability of the polypeptide. Polypeptides described herein can be made recombinantly, synthetically, or in tissue culture.

A CPX polypeptide or protein molecule, as defined above, is a circularly permuted variant of a bacterial outer membrane protein OmpX derived from bacteria, including, but not limited to *Escherichia coli, Shigella sonnei, Shigella dysenteriae, Shingella flexneri, Salmonella typhimurium, Salmonella enterica, Enterobacter aerogenes, Serratia marcescens, Yersinia pestis*, or *Klebsiella pneumoniae*. The molecule need not be physically derived from the particular isolate in question, but may be synthetically or recombinantly produced.

The amino acid sequences of a number of OmpX proteins are known. Representative sequences from bacteria are listed in the National Center for Biotechnology Information (NCBI) database. See, for example, NCBI entries: *Escherichia coli* OmpX, Accession No. P0A917; *Serratia marcescens* OmpX, Accession No. AAS78634; *Salmonella enterica* subsp. *enterica* serovar *Choleraesuis* str. SC-B67 ail and ompX homolog, Accession No. YP_219185; *Salmo-* nella enterica subsp. enterica serovar Typhi OmpX precursor, Accession No. CAD05280; Enterobacter cloacae OmpX, Accession No. P25253; Yersinia pseudotuberculosis IP 32953 OmpX, Accession No. YP_071052; Yersinia pseudotuberculosis IP 32953 OmpX, Accession No. YP_071052; Shigella flexneri OmpX precursor, Accession No. P0A920; Escherichia coli OmpX precursor, Accession No. P0A918; Escherichia coli OmpX precursor, Accession No. P0A919; Salmonella enterica subsp. enterica serovar Typhi Ty2 OmpX, Accession No. NP_805818; Shigella flexneri 2a str. 301 OmpX, Accession No. NP_706692; Yersinia pestis KIM OmpX, Accession No. NP_669000; Salmonella enterica subsp. enterica serovar Typhi str. CT18 OmpX, Accession No. NP_455368; Salmonella typhimurium LT2 OmpX, Accession No. NP_459810; Escherichia coli O157:H7 str. Sakai OmpX, Accession No. NP_308919; Escherichia coli O157:H7 EDL933 OmpX, Accession No. NP_286578; Shigella flexneri 2a str. 2457T OmpX, Accession No. NP_836469; Salmonella enterica subsp. enterica serovar Choleraesuis str. SC-B67 OmpX, Accession No. YP_215816; Yersinia pestis CO92 OmpX, Accession No. NP_406040; Yersinia pestis biovar Microtus str. 91001 OmpX, Accession No. NP_993650; Escherichia coli CFT073 OmpX, Accession No. NP_752830; Salmonella enterica subsp. enterica serovar Paratyphi A str. ATCC 9150 OmpX, Accession No. YP_151143; Erwinia carotovora subsp. atroseptica SCRI1043 OmpX, Accession No. YP_050855; Erwinia carotovora subsp. atroseptica SCRI1043 OmpX, Accession No. YP_050855; Escherichia coli APEC O1 OmpX precursor, Accession No. ABJ00194; Shigella boydii Sb227 OmpX, Accession No. YP_407207; Escherichia coli UTI89 OmpX, Accession No. ABE06304; Yersinia pestis KIM OmpX, Accession No. NP_669349; Yersinia pestis KIM OmpX, Accession No. NP_668646; Escherichia coli O157:H7 EDL933 OmpX, Accession No. AAG55186; Shigella flexneri 2a str. 2457T OmpX, Accession No. AAP16275; Escherichia coli APEC O1 OmpX precursor, Accession No. YP_851908; Escherichia coli UTI89 OmpX, Accession No. YP_539835; and Shigella sonnei Ss046 OmpX, Accession No. YP_309776; all of which sequences (as entered by the date of filing of this application) are herein incorporated by reference.

The term "passenger" polypeptide refers to a polypeptide linked to the N- or C-terminus of CPX or a variant thereof for display at the surface of a bacterial cell. Preferably, a passenger polypeptide is capable of interacting physically with arbitrary compositions of matter (biological or non-biological), and exhibits a biological activity (e.g., affinity, specificity, catalysis, assembly etc.) substantially similar to the corresponding free polypeptide in solution. In other words, the displayed passenger polypeptide interacts with or binds a given target molecule in a manner that is substantially similar to that when the polypeptide is in its native environment and not attached to CPX or a variant thereof.

As used herein, the term "ligand" refers to a molecule that binds to another molecule, e.g., an antigen binding to an antibody, a hormone or neurotransmitter binding to a receptor, or a substrate or allosteric effector binding to an enzyme and includes natural and synthetic biomolecules, such as proteins, polypeptides, peptides, nucleic acid molecules, carbohydrates, sugars, lipids, lipoproteins, small molecules, natural and synthetic organic and inorganic materials, synthetic polymers, and the like.

The term "polynucleotide", as known in the art, generally refers to a nucleic acid molecule. A "polynucleotide" can include both double- and single-stranded sequences and refers to, but is not limited to, prokaryotic sequences, eukaryotic mRNA, cDNA from viral, prokaryotic or eukaryotic mRNA, genomic RNA and DNA sequences from viral (e.g. RNA and DNA viruses and retroviruses), prokaryotic DNA or eukaryotic (e.g., mammalian) DNA, and especially synthetic DNA sequences. The term also captures sequences that include any of the known base analogs of DNA and RNA, and includes modifications such as deletions, additions and substitutions (generally conservative in nature), to the native sequence. These modifications may be deliberate, as through site-directed mutagenesis, or may be accidental, such as through mutations of hosts including polynucleotides encoding CPX or a variant thereof. Modifications of polynucleotides may have any number of effects including, for example, facilitating expression/bacterial display of the polypeptide product at the surface of a host cell.

A polynucleotide can encode a biologically active (e.g., CPX or a variant thereof) protein or polypeptide. Depending on the nature of the polypeptide encoded by the polynucleotide, a polynucleotide can include as little as 10 nucleotides, e.g., where the polynucleotide encodes a linker, tag or label, or an antigen or epitope for bacterial display. Typically, the polynucleotide encodes peptides of at least 10, 11, 12, 13, 14, 15, 16, 17, 18, 19, 20, 21, 22, 23, 24, 25, 30 or even more amino acids.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein, polypeptide, or peptide means a polypeptide produced by expression of a recombinant polynucleotide. In general, the gene of interest is cloned and then expressed in transformed organisms, as described further below. The host organism expresses the foreign gene to produce the protein under expression conditions.

A "polynucleotide coding sequence" or a sequence that "encodes" a selected polypeptide, is a nucleic acid molecule that is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus. A transcription termination sequence may be located 3' to the coding sequence. Typical "control elements," include, but are not limited to, transcription regulators, such as promoters, transcription enhancer elements, transcription termination signals, and polyadenylation sequences; and translation regulators, such as sequences for optimization of initiation of translation, e.g., Shine-Dalgarno (ribosome binding site) sequences, Kozak sequences (i.e., sequences for the optimization of translation, located, for example, 5' to the coding sequence), leader sequences (heterologous or native), translation initiation codon (e.g., ATG), and translation termination sequences. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is induced by an analyte, cofactor, regulatory protein, etc.), and constitutive promoters.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

By "isolated" is meant, when referring to a polynucleotide or a polypeptide, that the indicated molecule is separate and discrete from the whole organism with which the molecule is found in nature or, when the polynucleotide or polypeptide is not found in nature, is sufficiently free of other biological macromolecules so that the polynucleotide or polypeptide can be used for its intended purpose.

The terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof that is capable of exhibiting fluorescence in the detectable range. Particular examples of labels that may be used with the invention include, but are not limited to phycoerythrin, Alexa dyes, fluorescein, YPet, CyPet, Cascade blue, allophycocyanin, Cy3, Cy5, Cy7, rhodamine, dansyl, umbelliferone, Texas red, luminol, acradimum esters, biotin, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), firefly luciferase, Renilla luciferase, NADPH, beta-galactosidase, horseradish peroxidase, glucose oxidase, alkaline phosphatase, chloramphenical acetyl transferase, and urease.

The term "derived from" is used herein to identify the original source of a molecule but is not meant to limit the method by which the molecule is made which can be, for example, by chemical synthesis or recombinant means.

The terms "variant," "analog" and "mutein" refer to biologically active derivatives of the reference molecule that retain desired activity (e.g., efficient polypeptide display) as described herein. In general, the terms "variant" and "analog" refer to compounds having a native polypeptide sequence and structure with one or more amino acid additions, substitutions and/or deletions (e.g., in the linker joining native N- and C-terminii or at positions 165 and 166), relative to the native molecule, so long as the modifications do not destroy biological activity and which are "substantially homologous" to the reference molecule as defined below. In general, the amino acid sequences of such analogs will have a high degree of sequence homology to the reference sequence, e.g., amino acid sequence homology of more than 50%, generally more than 60%-70%, even more particularly 80%-85% or more, such as at least 90%-95% or more, when the two sequences are aligned. Often, the analogs will include the same number of amino acids but will include substitutions, as explained herein. The term "mutein" further includes polypeptides having one or more amino acid-like molecules including but not limited to compounds comprising only amino and/or imino molecules, polypeptides containing one or more analogs of an amino acid (including, for example, unnatural amino acids, etc.), polypeptides with substituted linkages, as well as other modifications known in the art, both naturally occurring and non-naturally occurring (e.g., synthetic), cyclized, branched molecules and the like. The term also includes molecules comprising one or more N-substituted glycine residues (a "peptoid") and other synthetic amino acids or peptides. (See, e.g., U.S. Pat. Nos. 5,831,005; 5,877,278; and 5,977,301; Nguyen et al., Chem Biol. (2000) 7:463-473; and Simon et al., Proc. Natl. Acad. Sci. USA (1992) 89:9367-9371 for descriptions of peptoids). Preferably, the analog or mutein has at least the same polypeptide display efficiency as the native OmpX molecule. Methods for making polypeptide analogs and muteins are known in the art and are described further below.

Analogs generally include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact. One of skill in the art may readily determine regions of the molecule of interest that can tolerate change by reference to Hopp/Woods and Kyte-Doolittle plots, well known in the art.

By "derivative" is intended any suitable modification of the native polypeptide of interest, of a fragment of the native polypeptide, or of their respective analogs, such as glycosylation, phosphorylation, polymer conjugation (such as with polyethylene glycol), or other addition of foreign moieties, so long as the desired biological activity of the native polypeptide is retained. Methods for making polypeptide fragments, analogs, and derivatives are generally available in the art.

By "fragment" is intended a molecule consisting of only a part of the intact full-length sequence and structure. The fragment can include a C-terminal deletion an N-terminal deletion, and/or an internal deletion of the peptide. Active fragments of a particular protein or peptide will generally include at least about 5-10 contiguous amino acid residues of the full-length molecule, preferably at least about 15-25 contiguous amino acid residues of the full-length molecule, and most preferably at least about 20-50 or more contiguous amino acid residues of the full-length molecule, or any integer between 5 amino acids and the full-length sequence, provided that the fragment in question retains biological activity, such as ligand-binding activity, as defined herein.

"Substantially purified" generally refers to isolation of a substance (compound, polynucleotide, protein, polypeptide, polypeptide composition) such that the substance comprises the majority percent of the sample in which it resides. Typically in a sample a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

"Homology" refers to the percent identity between two polynucleotide or two polypeptide moieties. Two nucleic acid, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence identity over a defined length of the molecules. As used herein, substantially homologous also refers to sequences showing complete identity to the specified sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules (the reference sequence and a sequence with unknown % identity to the reference sequence) by aligning the sequences, counting the exact number of matches between the two aligned sequences, dividing by the length of the reference sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

II. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The purpose of "cell surface display" systems is to present polypeptides on living cells to extracellular targets of any size and molecular composition. The application of bacterial display technology to a broad range of protein engineering applications, however, has been hindered by the absence of robust, validated display scaffolds. The present invention is based on the discovery of novel CPX variants with enhanced properties for use in bacterial display.

The construction of a circularly permuted outer membrane protein OmpX (CPX) for use as a protein scaffold for polypeptide display was described earlier (see U.S. patent application Ser. No. 10/920,244, which is herein incorporated by reference in its entirety). The original CPX protein had the unique characteristic that both C- and N-termini of the scaffold were localized on the bacterial cell surface and available for display of polypeptides and peptides. The CPX protein scaffold consisted of the native OmpX signal sequence, which is cleaved after translocation; a sequence with an embedded SfiI restriction site (GQSGQ) (SEQ ID NO: 35) after which peptides may be inserted; a flexible linking sequence (GGQSGQ) (SEQ ID NO:28); amino acids S54-F148 of the mature OmpX; a GGSG (SEQ ID NO:2) linker joining the native C- and N-termini; and amino acids A1-S53 of the mature OmpX. This previously described CPX protein unfortunately exhibited reduced surface localization compared to OmpX, which interfered with the presentation of large peptides and the display of two unique peptides simultaneously from structurally adjacent termini.

As described in Experimental Examples 1-4, semi-rational design and directed evolution were used to create circularly permuted outer membrane protein variants also presenting both the N- and C-termini, but showing significantly enhanced display of a diverse group of peptides, microproteins, and repeat proteins compared to CPX. In order to identify CPX scaffold variants with increased display efficiency, libraries of CPX variants were constructed and screened for optimal linker sequences joining the native N- and C-termini of OmpX and for fortuitous mutations that more efficiently display peptides. More generally, this approach provides a potential route to enhance the performance of a variety of cell surface display scaffolds in presenting passenger proteins. Thus, the methods described herein can be used to make library screens more efficient and less biased towards peptides that are difficult to display.

In order to further an understanding of the invention, a more detailed discussion is provided below regarding the construction of CPX variants having enhanced display properties and their use in bacterial display applications.

A. Circularly Permuted OmpX Variants

Circularly permuted variants, as described herein, can be constructed for any bacterial outer membrane protein OmpX. Representative OmpX sequences from various species of bacteria are known and listed herein. Thus, circulated permuted variants can be derived from any bacterial strain or isolate, including, but not limited to *Escherichia coli, Shigella sonnei, Shigella dysenteriae, Shingella flexneri, Salmonella typhimurium, Salmonella enterica, Enterobacter aerogenes, Serratia marcescens, Yersinia pestis,* or *Klebsiella pneumoniae*. Representative OmpX sequences from bacteria include: *Escherichia coli* OmpX, Accession No. P0A917; *Serratia marcescens* OmpX, Accession No. AAS78634; *Salmonella enterica* subsp. *enterica* serovar *Choleraesuis* str. SC-B67 ail and ompX homolog, Accession No. YP_219185; *Salmonella enterica* subsp. *enterica* serovar *Typhi* OmpX precursor, Accession No. CAD05280; *Enterobacter cloacae* OmpX, Accession No. P25253; *Yersinia pseudotuberculosis* IP 32953 OmpX, Accession No. YP_071052; *Yersinia pseudotuberculosis* IP 32953 OmpX, Accession No. YP_071052; *Shigella flexneri* OmpX precursor, Accession No. P0A920; *Escherichia coli* OmpX precursor, Accession No. P0A918; *Escherichia coli* OmpX precursor, Accession No. P0A919; *Salmonella enterica* subsp. *enterica* serovar *Typhi* Ty2 OmpX, Accession No. NP_805818; *Shigella flexneri* 2a str. 301 OmpX, Accession No. NP_706692; *Yersinia pestis* KIM OmpX, Accession No. NP_669000; *Salmonella enterica* subsp. *enterica* serovar *Typhi* str. CT18 OmpX, Accession No. NP_455368; *Salmonella typhimurium* LT2 OmpX, Accession No. NP_459810; *Escherichia coli* O157:H7 str. Sakai OmpX, Accession No. NP_308919; *Escherichia coli* O157:H7 EDL933 OmpX, Accession No. NP_286578; *Shigella flexneri* 2a str. 2457T OmpX, Accession No. NP_836469; *Salmonella enterica* subsp. *enterica* serovar *Choleraesuis* str. SC-B67 OmpX, Accession No. YP_215816; *Yersinia pestis* CO92 OmpX, Accession No. NP_406040; *Yersinia pestis* biovar *Microtus* str. 91001 OmpX, Accession No. NP_993650; *Escherichia coli* CFT073 OmpX, Accession No. NP_752830; *Salmonella enterica* subsp. *enterica* serovar *Paratyphi* A str. ATCC 9150 OmpX, Accession No. YP_151143; *Erwinia carotovora* subsp. *atroseptica* SCRI1043 OmpX, Accession No. YP_050855; *Erwinia carotovora* subsp. *atroseptica* SCRI1043 OmpX, Accession No. YP_050855; *Escherichia coli* APEC O1 OmpX precursor, Accession No. ABJ00194; *Shigella boydii* Sb227 OmpX, Accession No. YP_407207; *Escherichia coli* UTI89 OmpX, Accession No. ABE06304; *Yersinia pestis* KIM OmpX, Accession No. NP_669349; *Yersinia pestis* KIM OmpX, Accession No. NP_668646; *Escherichia coli* O157:H7 EDL933 OmpX, Accession No. AAG55186; *Shigella flexneri* 2a str. 2457T OmpX, Accession No. AAP16275; *Escherichia coli* APEC O1 OmpX precursor, Accession No. YP_851908; *Escherichia coli* UTI89 OmpX, Accession No. YP_539835; and *Shigella sonnei* Ss046 OmpX, Accession No. YP_309776; all of which sequences (as entered by the date of filing of this application) are herein incorporated by reference. Any of these sequences or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, can be used to construct a CPX variant, as described herein.

Bacterial display can be used in combination with magnetic-activated cell sorting (MACS) and fluorescence-activated cell sorting (FACS) techniques for quantitative library analysis and screening for CPX variants that display polypeptides or peptides efficiently (see, e.g., Examples 1-4 and Rice et al. (2006) Protein Sci. 15:825-836; U.S. Patent Application Publication No. 2005/0196406; Daugherty et al. (2000) J. Immuunol. Methods 243(1-2):211-2716; Georgiou (2000) Adv. Protein Chem. 55:293-315; Daugherty et al. (2000) Proc. Natl. Acad. Sci. U.S.A. 97(5):2029-3418; Olsen et al. (2003) Methods Mol. Biol. 230:329-342; and Boder et al. (2000) Proc. Natl. Acad. Sci. U.S.A. 97(20): 10701-10705; herein incorporated by reference in their entireties). Analysis of the display efficiency of a CPX variant is facilitated by the use of a passenger polypeptide comprising a label (e.g., phycoerythrin, Alexa dye, fluorescein, YPet, CyPet) that allows detection of the displayed polypeptide at the bacterial cell surface.

The sequences of exemplary CPX variants for use in bacterial display are described in the table below:

| Clone | Positions 165 | 166 | Linker |
|---|---|---|---|
| CPX | A | G | GGSG (SEQ ID NO: 2) |
| CPX-3X-1 | A | G | GRK (SEQ ID NO: 3) |
| CPX-3X-2 | A | G | GRK (SEQ ID NO: 3) |
| CPX-3X-3 | A | G | GTK (SEQ ID NO: 4) |
| CPX-3X-4 | A | G | GKK (SEQ ID NO: 5) |
| CPX-4X-1 | A | G | GSKR (SEQ ID NO: 6) |
| CPX-4X-2 | A | G | GRQK (SEQ ID NO: 7) |
| CPX-4X-3 | A | G | SWPN (SEQ ID NO: 8) |
| CPX-4X-4 | V | G | PRKS (SEQ ID NO: 9) |
| CPX-5X-1 | A | G | GRTRK (SEQ ID NO: 10) |
| CPX-5X-2 | A | G | GRKRN (SEQ ID NO: 11) |
| CPX-5X-3 | V | G | GATRR (SEQ ID NO: 12) |
| CPX-5X-4 | A | S | GSQSK (SEQ ID NO: 13) |
| CPX-6X-1 | A | G | GTKRYH (SEQ ID NO: 14) |

-continued

| Clone | Positions 165 | 166 | Linker |
|---|---|---|---|
| CPX-6X-2 | A | G | GRRHYK (SEQ ID NO: 15) |
| CPX-6X-3 | A | G | GNRRHR (SEQ ID NO: 16) |
| CPX-6X-4 | A | S | GSKQSK (SEQ ID NO: 17) |
| CPX-L2-1 | L | S | GSKSRR (SEQ ID NO: 18) |
| CPX-L2-2 | F | S | GRKNSH (SEQ ID NO: 19) |
| CPX-L2-3 | I | S | GTRGSQ (SEQ ID NO: 20) |
| CPX-L2-4 | L | S | GHRSHR (SEQ ID NO: 21) |
| CPX-L2-5 | I | S | GDRKRR (SEQ ID NO: 22) |
| CPX-L2-6 | V | A | GARGRH (SEQ ID NO: 23) |
| CPX-L2-7 | V | S | GTHNSQ (SEQ ID NO: 24) |
| CPX-L2-8 | V | S | GPNKSR (SEQ ID NO: 25) |
| CPX-L2-9 | I | S | GPHNSR (SEQ ID NO: 26) |
| CPX-L2-10 | I | S | HRGYHAQR (SEQ ID NO: 27) |

As shown in Examples 1-4, CPX variants that efficiently displayed polypeptides were identified by screening libraries of OmpX polypeptides containing different linkers between the native N- and C-terminii. In order to identify CPX scaffold variants with optimal linker sequences joining the native C- and N-termini, four separate libraries with three, four, five or six random linker amino acids were screened using MACS and FACS. CPX variants as described herein revealed a preference for longer linkers of five to six residues, a consensus for glycine at the first position of the linker, and an abundance of basic residues in the remaining positions.

Thus, in one aspect, the invention includes a CPX variant comprising a linker joining the native N-terminus and C-terminus, wherein the linker is 3-8 residues in length and comprises a glycine and one or more basic amino acids. In a preferred embodiment, the first residue of the linker is a glycine. In certain embodiments, the linker comprises at least two basic residues, for example, at least two arginine residues or two lysine residues, or at least one arginine residue and at least one lysine residue. In preferred embodiments the linker is 5 or 6 residues in length. In one embodiment, the linker is 6 residues in length and the first residue of the linker is a glycine and the third and sixth residues of the linker are selected from the group consisting of arginine, lysine, serine, histidine, glutamine, and asparagine. In certain embodiments, the linker comprises a sequence selected from the group consisting of SEQ ID NOS:2-27.

In addition, CPX variants can be screened for fortuitous mutations that enhance the display efficiency of a passenger polypeptide. As shown in Example 2, substitutions at positions 165 and 166 (numbered relative to the reference sequence of SEQ ID NO:1) near the native C-terminus of OmpX greatly increased display levels of polypeptides. Thus, the CPX variants described herein may comprise one or more mutations that increase the display efficiency of a passenger polypeptide. In certain embodiments, a hydrophobic residue is substituted at the position corresponding to A165 of the native OmpX protein (numbered relative to the reference sequence of SEQ ID NO:1), for example, a valine, leucine, isoleucine, or phenylalanine. In another embodiment, the amino acid at the position corresponding to G166 (numbered relative to the reference sequence of SEQ ID NO:1) of the native OmpX protein is replaced, for example, with a serine or alanine. In a preferred embodiment, the CPX variant comprises the mutations A165L and G166S and a linker consisting of the sequence of GSKSRR (SEQ ID NO:18).

A CPX variant can display a single passenger polypeptide on either the N-terminus or the C-terminus. Alternatively, a CPX variant can display two passenger polypeptides simultaneously on both the N- and C-termini. Preferably, a passenger polypeptide is capable of interacting physically with arbitrary compositions of matter (biological or non-biological), and exhibits a biological activity (e.g., affinity, specificity, catalysis, assembly etc.) substantially similar to the corresponding free polypeptide in solution. In other words, the displayed passenger polypeptide interacts with or binds a given target molecule in a manner that is substantially similar to that when the polypeptide is in its native environment and not attached to the CPX protein or a variant thereof.

Biterminal display has numerous advantages, including the ability to quantify the amount of the CPX variant displayed on the cell surface and to screen libraries on both termini simultaneously. For this purpose, a CPX variant can be loaded with a single labeled passenger polypeptide or two differently labeled passenger polypeptides in order to allow detection of surface display. The quantification of the display level during library screening by labeling of a passenger polypeptide allows for polypeptides with a high affinity but low display level to be differentiated from polypeptides with a high display level but moderate affinity. Moreover, biterminal display allows for the possibility of creating peptide libraries on each terminus where both peptides can bind to separate regions of the same protein target, causing increased binding affinity and specificity through avidity.

Additionally, linkers may be inserted between a passenger polypeptide of interest and either the N- or C-terminus of the CPX variant to which it is connected in order to avoid steric hindrance between simultaneously displayed passenger polypeptides and/or their binding partners. For example, a long flexible linker comprising multiple repeats of the sequence GGGS (SEQ ID NO:37) (e.g., (GGGS)$_4$ (SEQ ID NO:38), (GGGS)$_5$ (SEQ ID NO:34), or (GGGS)$_6$ (SEQ ID NO:39)) can be used to increase the accessibility of proteins to ligands and to avoid steric hindrance when using biterminal display.

Polynucleotides Encoding CPX Variants and Library Construction

Polynucleotides encoding CPX variants of the present invention can be produced in any number of ways, all of which are well known in the art.

In one embodiment, the polynucleotides are generated using recombinant techniques, well known in the art. One of skill in the art could readily determining nucleotide sequences that encode the desired CPX variants using standard methodology and the teachings herein.

Oligonucleotide probes can be devised based on the known sequences of OmpX proteins and used to probe genomic or cDNA libraries. The sequences can then be further isolated using standard techniques and, e.g., restriction enzymes employed to truncate the gene at desired portions of the full-length sequence. Similarly, sequences of interest can be isolated directly from cells and tissues containing the same, using known techniques, such as phenol extraction and the sequence further manipulated to produce the desired CPX variants. See, e.g., Sambrook et al., supra, for a description of techniques used to obtain and isolate DNA.

The sequences encoding the CPX variants can also be produced synthetically, for example, based on the known sequences. The nucleotide sequence can be designed with the appropriate codons for the particular amino acid sequence desired. The complete sequence is generally assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311; Stemmer et al. (1995) *Gene* 164:49-53.

Recombinant techniques are readily used to clone sequences encoding CPX variants useful in the claimed invention that can then be mutagenized in vitro by the replacement of the appropriate base pair(s) to result in the codon for the desired amino acid. Such a change can include as little as one base pair, effecting a change in a single amino acid, or can encompass several base pair changes. Alternatively, the mutations can be effected using a mismatched primer that hybridizes to the parent nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. See, e.g., Innis et al, (1990) PCR Applications: Protocols for Functional Genomics; Zoller and Smith, *Methods Enzymol.* (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al. *Proc. Natl. Acad. Sci USA* (1982) 79:6409.

Once coding sequences have been isolated and/or synthesized, they can be cloned into any suitable vector or replicon for expression in bacteria. (See Examples). The invention also includes expression constructs for expressing a given passenger polypeptide as an N-terminal fusion protein, a C-terminal fusion protein, or biterminal fusion protein, i.e., linked or fused directly to the CPX protein present on the external surface of a bacterial cell. Display and expression of a passenger polypeptide as an N-terminal or C-terminal or biterminal fusion with a CPX variant is accomplished by topological permutation of an OmpX protein as described in U.S. patent application Ser. No. 10/920,244, which is herein incorporated by reference. Sequence rearrangement of an OmpX protein can be accomplished using overlap extension PCR methods known in the art in order to create either an N-terminal or C-terminal fusion construct, or alternatively, a biterminal fusion construct. See Ho, et al. (1989) Gene 77(1):51-59, which is herein incorporated by reference. As will be apparent from the teachings herein, a wide variety of vectors encoding CPX variants coupled to one or more passenger polypeptides can be generated by creating expression constructs which operably link, in various combinations, polynucleotides encoding CPX variants and passenger polypeptides.

Numerous cloning vectors are known to those of skill in the art, and the selection of an appropriate cloning vector is a matter of choice. Examples of recombinant DNA vectors for cloning include pBAD33, pB30D, pBR322, pACYC177, pKT230, pGV1106, pLAFR1, pME290, pHV14, pBD9, pIJ61, and pUC6. See, generally, *DNA Cloning*: Vols. I & II, supra; Sambrook et al., supra; B. Perbal, supra.

The gene can be placed under the control of a promoter, ribosome binding site (for bacterial expression) and, optionally, an operator (collectively referred to herein as "control" elements), so that the DNA sequence encoding the desired CPX variant and passenger polypeptide(s) is transcribed into RNA in the host cell transformed by a vector containing this expression construction. The coding sequence may contain a naturally occurring OmpX signal peptide sequence or a heterologous signal sequence (e.g., from another outer membrane protein such as OmpA, OmpT, OmpC, OmpF, OmpN, LamB, FepA, FecA, or the like) to promote expression of the CPX variant at the surface of a bacterial host cell.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound (e.g., a regulatable promoter for controlled transcription).

In a preferred embodiment, a vector comprising the regulatable promoter araBAD is used to control transcription. Expression and display of the polypeptide is then accomplished by induction of protein expression by contacting with arabinose, preferably for about 10 to about 60 minutes, and more preferably for about 10 to about 20 minutes at 25° C. Controlling expression and display minimizes potential avidity effects that can result from excessive surface concentration of the displayed peptide.

Expression vectors of the present invention may also utilize a low copy origin of replication (e.g., p15A) in order to minimize the metabolic burden on the bacterial host cell such that the clonal representation of the polypeptide library is not affected by growth competition during library propagation. Additionally, expression vectors of the present invention may include a selectable marker such as an antibacterial resistance gene to a bacteriocidal antibiotic (e.g., chloramphenicol acetyltransferase, beta lactamase, or the like).

The control sequences and other regulatory sequences may be ligated to the coding sequence prior to insertion into a vector. Alternatively, the coding sequence can be cloned directly into an expression vector that already contains the control sequences and an appropriate restriction site.

In some cases it may be necessary to modify the coding sequence so that it may be attached to the control sequences with the appropriate orientation; i.e., to maintain the proper reading frame. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; *DNA Cloning*, Vols. I and II, supra; *Nucleic Acid Hybridization*, supra.

The expression vector is then used to transform an appropriate bacterial host cell. A number of bacterial hosts are known in the art, including but not limited to, *Escherichia coli, Shigella sonnei, Shigella dysenteriae, Shingella flexneri, Salmonella typhimurium, Salmonella enterica, Enterobacter aerogenes, Serratia marcescens, Yersinia pestis*, or *Klebsiella pneumoniae*, which will find use with the present expression constructs.

In preferred embodiments, a bacterial strain is chosen that is deficient in proteolytic machinery in order to prevent protein degradation See Meerman, H. J., Nature Biotechnol. 12(11):1107-1110, which is herein incorporated by reference. In some embodiments, a bacterial strain that makes truncated or otherwise modified lipopolysacharides on its surface may be used to minimize steric effects upon binding to large biomolecules including proteins, viruses, cells, and the like. In some preferred embodiments, the bacterial host has a genotype that aids the expression vector in regulating more tightly the production of the polypeptide to be displayed. The bacterial host may be modified using methods known in the art, including random mutagenesis, DNA shuffling, genome shuffling, gene addition libraries, and the like.

As exemplified herein, *Escherichia coli* strain, MC1061 is a suitable bacterial host for display of passenger polypeptides using CPX variants of the invention. The MC1061 strain exhibits (1) high transformation efficiency of greater than about $5 \times 10^9$ per microgram of DNA, (2) a short doubling time, i.e., 40 minutes or less, during exponential growth phase, (3) high level display of the given polypeptide, and (4) effective maintenance of the expression ON and OFF states (see Example 1).

In preferred embodiments, the expression vectors and libraries of the present invention incorporate (1) the use of a regulatable expression vector that allows on-off control of the production of the CPX protein or variant thereof, (2) efficient restriction sites immediately adjacent to a randomized site for insertion of cloned DNA encoding a random passenger polypeptide fused to the N-terminus, C-terminus or both terminii of the CPX variant to facilitate library construction, (3) time and temperature-controlled induction periods to obtain optimal display levels that result in higher quality results, (4) the use of a bacterial strain having a high plasmid transformation efficiency for transformation, (5) the use of optimized library construction protocols to construct large libraries, (6) the use of multiple-plasmid transformation to yield a larger number of unique passenger polypeptides for a given number of host cells, (7) the use of cell concentration to enable complete processing of larger numbers of sequences (e.g., $10^{11}$), or (8) any combination thereof.

In some embodiments of the present invention, a DNA library is constructed containing preferably greater than about $10^8$ sequences, and preferably more than about $10^{10}$ unique sequence members, using methods known in the art. This library size is preferred since library size has been shown to correlate with the quality (affinity and specificity) of the selected sequences. See Griffiths, A. D. and D. S. Tawfik (2000) Curr. Opin. Biotechnol. 11(4):338-53, which is herein incorporated by reference.

In some embodiments, a polypeptide library may be prepared by introduction and expression of nucleic acid sequences which encode polypeptides having about 1 to about 1000, preferably about 2 to about 30 amino acids in length. In certain embodiments, high DNA concentrations of more than about 0.1 µg per µl are used during transformation such that the transformed host cell contains one or more independent plasmid molecules. Transformation with multiple plasmids yields a larger number of unique peptides in the same volume of liquid, providing better overall results than when transformation is performed with only one molecule per cell. In some embodiments, a mixture of a plurality of different expression vectors and/or plasmids may be employed, for example, to allow cooperative binding of two different displayed peptides on the same surface, or to present a protein having multiple subunits, and the like.

A desired number of polypeptides may be displayed for different purposes. As exemplified herein, the method of the present invention utilizes an induction period of about 10 minutes to 6 hours to control total expression levels of the display polypeptide and the mode of the subsequent screen or selection such that the level of expression has no measurable effect upon the cell growth rate. In some embodiments, shorter time periods may be used to reduce avidity effects in order to allow selection of high affinity monovalent interactions. As provided herein, the ability to control display speeds the process and yields higher quality results, e.g., sequences that bind to a target with higher affinity.

In some embodiments, a cell concentration by a factor of about 10 may be used to enable complete processing of the entire pool of diversity in a volume of about 10 to about 100 ml. The library may be expanded by propagation by a factor of more than about 100-fold under conditions which prevent synthesis of the library elements, for example, with glucose to repress araBAD or lac promoters, and aliquots of the library may be prepared to represent a number of clones which is more than about three fold greater than the total number of library members.

For library selection, a subset of the total library, either randomly divided, or chosen for specific properties could be used as a starting point for screening. Either MACS and/or FACS methods known in the art may be used. Alternatively, methods known in the art that enable physical retention of desired clones and dilution or removal of undesired clones may be used. For example, the library may be grown in a chemostat providing continuous growth, diluting out only those cells that do not bind to a capture agent retained in the vessel. Alternatively, hosts may be cultured with medium having ingredients that promote growth of desired clones.

Cell sorting instrumentation is applied as a quantitative library screening tool to isolate the highest affinity clones from a magnetically enriched population. Two different approaches can be applied for quantitative screening on the basis of either equilibrium binding affinity (Equilibrium Screen) or dissociation rate constants (Kinetic Screen). See Daugherty, P. S., et al. (2000) J. Immunol. Methods 243(1-2):211-227; and Boder, E. T. and K. D. Wittrup (1998) Biotechnology Progress 14(1):55-62, which are herein incorporated by reference in their entireties. For equilibrium screening, cell populations are labeled with limiting concentrations of the target proteins, and all cells exhibiting fluorescence intensities above background autofluorescence are collected.

Instead of using random synthetic peptides to provide genetic diversity, fragment genomic DNA of varying lengths, cDNA of varying lengths, shuffled DNAs, and consensus generated sequences may be employed in accordance with the present invention.

Non-natural amino acids having functionality not represented among natural amino acids, e.g., metal binding, photoactivity, chemical functionality, and the like, may be displayed on the surface using a suitable bacterial host. In this case, the library or an equivalent library may be transformed into strains engineered to produced non-natural amino acids. See Kiick, K. L. et al. (2001) FEBS Lett. 502(1-2):25-30; Kiick, K. L., et al. (2002) PNAS USA 99(1):19-24; Kirshenbaum, K., et al. (2002) Chembiochem. 3(2-3):235-237; and Sharma, N., et al. (2000) FEBS Lett. 467(1):37-40, which are herein incorporated by reference. Peptides incorporating non-natural amino acids are isolated by selection or screening for functions which require inclusion of the non-natural monomers into the displayed polypeptide.

Displayed polypeptides may be made to include post-translation modifications, including glyocosylation, phosphorylation, hydroxylation, amidation, and the like, by introduction of a gene or set of genes performing the desired modifications into the strain used for screening and selection, e.g., MC1061 or comparable host strain. Genes performing such post-translational modifications may be isolated from cDNA or genomic libraries by cotransformation with the library and screening for the desired function using FACS or another suitable method. For example, post-translational glycosylation activities (enzymes) can be found co-transforming.

The polypeptides displayed by CPX or a variant thereof preferably possess a length that preserves the folding and export of the carrier protein while presenting significant sequence and structural diversity. In some embodiments, the CPX or variant thereof used as a carrier protein may be modified by rational redesign or directed evolution by the methods described herein to increase levels of display or enhance polypeptide presentation. For example, the linker between the native N- and C-terminii of OmpX may be optimized by random point or cassette mutagenesis and screened for enhanced presentation (see, e.g., Examples 1-4). In addition, mutations may be incorporated into the CPX scaffold that increase the display efficiency of a passenger polypeptide (e.g., substitutions at positions 165 and 166).

Terminal fusion display allows for high mobility of the surface displayed molecule, increased accessibility to target molecules, and simple proteolytic cleavage of the displayed peptide for production of soluble peptides. Terminal fusion display also enables the identification of novel substrates and ligands, e.g., for proteases, peptidases, kinases, receptors, and antibodies. The expression vectors according to the present invention provide a direct way for enhancing the conformational diversity and surface mobility of surface anchored peptides and polypeptides. Through the increased mobility resulting from terminal fusion (as opposed to insertional fusions), the apparent affinity of a polypeptide binding to its corresponding target molecule or material more closely resembles that of the peptide in solution. The N-terminal or C-terminal or biterminal display vectors allow the retention of an energetically stable outer membrane protein structure, compatible with folding, transport, and assembly for efficient display of a given passenger polypeptide on the bacterial cell surface.

In some embodiments, a cDNA library may be cloned into the display position of the N-terminal or C-terminal or biterminal fusion expression vector, with a terminal affinity tag, such as a T7 tag epitope, or a label, or the like, appended to a terminus of the cDNA clone allowing for measurement of the total display level on the cell surface. As used herein, the term "affinity tag" refers to a biomolecule, such as a polypeptide segment, that can be attached to a second biomolecule to provide for purification or detection of the second biomolecule or provide sites for attachment of the second biomolecule to a substrate. Examples of affinity tags include a poly-histidine tract, protein A (Nilsson et al. (1985) EMBO J. 4:1075; Nilsson et al. (1991) Methods Enzymol. 198:3, glutathione S transferase (Smith and Johnson (1988) Gene 67:31), Glu-Glu affinity tag (Grussenmeyer et al., (1985) PNAS USA 82:7952), substance P, FLAG peptide (Hopp et al. (1988) Biotechnology 6:1204), streptavidin binding peptide, or other antigenic epitope or binding domain, and the like, (Ford et al. (1991) Protein Expression and Purification 2:950), all of which are herein incorporated by reference. As used herein, a "label" is a molecule or atom which can be conjugated to a biomolecule to render the biomolcule or form of the biomolecule, such as a conjugate, detectable or measurable. Examples of labels include chelators, photoactive agents, radioisotopes, fluorescent agents, paramagnetic ions, and the like.

The presence of surface localized proteins may be monitored using an antibody or reagent specific for the tag or label according to methods known in the art. Cells binding to a target protein may be then selected using MACS and/or FACS. The library pool may be incubated with a fluorescent label of one color (such as green) and then a second fluorescent label of a second color (such as red) to identify the presence of a full length cDNA of interest. Clones which are red and green are then isolated from the library directly using cell sorting methods known in the art.

In some embodiments, the polypeptides of an N-terminal, C-terminal, or biterminal fusion expression vector may be isolated or purified from the outer surface of the host. In other words, a polypeptide may be expressed using an N-terminal, C-terminal, or biterminal fusion expression vector and then produced in a soluble form (free in solution) by introducing a suppressible codon downstream of the given polypeptide. Alternatively, a protease susceptible linker may be used in place of the "suppressible" codon. The polypeptides are displayed on the surface at high density by induction, such as with arabinose for a period of about 2 hours. The cells are washed once or twice in a compatible buffer, such as PBS, to remove undesired proteins and other debris, the cells are concentrated, and a protease is added to the cell suspension. The proteolytically cleaved polypeptide is then harvested by removal of the bacteria by low-speed centrifugation, and transfer of the supernatant into a fresh tube.

C. Applications

The present invention may be broadly applied to methods to isolate, enhance or otherwise alter, peptide and polypeptide sequences that perform useful or desired functions including binding, catalysis, assembly, transport, and the like. For example, the expression vectors of the present invention may be used to isolate peptide molecular transformation catalysts, develop whole-cell reagents, discover peptides that promote self assembly, discover in vivo targeting peptides for drug and gene delivery, discover and increase peptides binding to materials surfaces, e.g., semiconductors, mapping proteins such as protein contacts, and biomolecular networks, identifying enzyme substrates/inhibitors, identifying receptor agonists/antagonists, isolating inhibitors of bacterial or viral pathogenesis, discovering peptides that mediate endocytosis and cellular entry, mapping antibody and protein epitopes including multiplex mapping, identifying peptide mimics of non-peptide ligands, and isolating metal binding peptides, e.g., for bioremediation, nano-wire synthesis, according to methods known in the art. See Georgiou, G., et al. (1997) Nat. Biotechnol. 15(1):29-34; Pasqualini, R. and E. Ruoslahti (1996) Nature 380(6572):364-366; Whaley, S. R., et al. (2000) Nature 405(6787):665-668; Fields, S. and R. Sternglanz (1994) Trends in Genetics 10(8):286-292; Kim, W. C., et al. (2000) J. Biomol. Screen. 5(6):435-440; Yang, W. P., et al. (1995)

J. Mol. Biol. 254(3): 392-403; Poul, M. A., et al. (2000) J. Mol. Biol. 301(5):1149-1161; James, L. C., et al. (2003) Science 299(5611):1362-1367; Feldhaus, M. J., et al. (2003) Nat. Biotechnol. 21(2):163-170; Kjaergaard, K., et al. (2001) Appl. Environ. Microbiol. 67(12):5467-5473, and Shusta, E. V., et al. (1999) Curr. Opin. Biotechnol. 10(2): 117-122, which are herein incorporated by reference in their entireties.

Thus, in one embodiment, CPX variants of the invention can be used in display libraries for screening polypeptides for biological activity. A polypeptide display library, as described herein, is provided comprising CPX variants carrying a plurality of passenger polypeptides displayed on bacterial cells. The polypeptides are contacted with a target molecule of interest and assayed for biological activity in the presence of the target molecule in order to identify displayed passenger polypeptides that have biological activity. For this purpose, any CPX variant described herein can be used in the polypeptide display library for screening polypeptides. The polypeptide display library can include passenger polypeptides fused to the N- or C- or both terminii of the CPX variants. The biological activity assayed can be enzymatic activity, substrate activity, ligand-binding activity, agonist activity, antagonist activity, transport activity, or any other biological activity. Any target molecule can be chosen, including but not limited to, a receptor, a ligand, an antibody, an antigen, an enzyme, a transporter, a substrate, an inhibitor, an activator, a cofactor, a drug, a nucleic acid, a lipid, a carbohydrate, a glycoprotein, a small organic molecule, or an inorganic molecule.

In certain embodiments, the invention includes a method of screening a library of polypeptides for the ability to bind to a target molecule, the method comprising: a) providing a polypeptide display library comprising CPX variants carrying a plurality of passenger polypeptides displayed on bacterial cells, b) contacting the plurality of passenger polypeptides with the target molecule, and c) identifying at least one displayed passenger polypeptide that binds to the target molecule.

The target molecule may comprise a detectable label in order to facilitate detection of binding of the target molecule to the displayed polypeptides. Detectable labels suitable for use in the present invention include any composition detectable by spectroscopic, photochemical, biochemical, immunochemical, electrical, optical, or chemical means. Useful labels in the present invention include biotin or other streptavidin-binding proteins for staining with labeled streptavidin conjugate, magnetic beads (e.g., Dynabeads™), fluorescent dyes (e.g., phycoerythrin, YPet, fluorescein, texas red, rhodamine, green fluorescent protein, and the like, see, e.g., Molecular Probes, Eugene, Oreg., USA), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

In some embodiments, the N-terminal, C-terminal, or biterminal fusion expression vectors of the present invention can be used for the identification of substrates, such as protease or kinase substrates, from substrate libraries. Accordingly, an expression vector may be modified to express a fluorescent protein using methods known in the art. For example, the use of a bicistronic expression vector comprising a CPX variant, (2) a ribosomal binding site down stream of the CPX variant sequence, and (3) a label such as a green fluorescent protein suitable for efficient detection using fluorescence activated cell sorting (e.g., alajGFP). Expression is then monitored through the intensity of green fluorescence.

For example, a library of protease or peptide substrates is created using methods known in the art. The substrates are fused to the N-terminus or C-terminus or both terminii of CPX variants using an expression vector expressing a green fluorescent protein. The substrate library is constructed such that a label or an affinity tag suitable for fluorescence labeling is fused to the free terminus of a passenger polypeptide on the cell surface. Host cells expressing the substrate library labeled with a red fluorescent protein are grown, and cells which are green but not red are removed from the population to eliminate the isolation of false positive clones. The library is then incubated with an enzyme (e.g., a protease or peptidase), and cells which loose red fluorescence while retaining green fluorescence are isolated from the population using FACS.

In some embodiments, the N-terminal, C-terminal, or biterminal fusion expression vectors of the present invention may be used to construct whole cells that can be used as reagents. For example, one or more peptides identified using the methods herein, binding to a protein, virus, or cellular receptor, or synthetic composition of matter, are displayed on the outer surface of a bacterial cell at a desired surface density. Cells can then be coupled directly to a material, e.g., glass/silicon, gold, polymer, by virtue of peptides selected to bind these materials, and used to capture in solution molecules binding to various other displayed peptides on the same cell. For optical detection, cells can co-express a fluorescent or luminescent reporter molecule such GFP, or luciferase. Flow cytometry, or fluorescence microscopy can be used to detect binding of molecular recognition element displaying cells to the target agent, e.g., virus, cell, particle, bead, and the like.

The polypeptide display systems of the present invention allow the creation of renewable whole cell binding reagents in non-specialized laboratories since this method is technically accessible and libraries are reusable. This approach has already proven useful for selecting cell-specific binding peptides, and for performing diagnostic assays using flow cytometry and fluorescence microscopy. Furthermore, the surface displayed polypeptides can be used for parallel or multiplex ligand isolation, and clones can be processed with efficient single-cell deposition units present on many cell sorters. See Feldhaus, M. J., et al. (2003) Nat. Biotechnol. 21(2):163-170, which is herein incorporated by reference. Consequently, the expression vectors of the present invention may be used in proteomic applications including proteome-wide ligand screens for protein-detecting array development See Kodadek, T. (2001) Chem. Biol. 8(2):105-115, which is herein incorporated by reference.

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1: Materials and Methods

Bacterial Strains, Reagents and Plasmids

All experiments were performed with *E. coli* strain MC1061 (F-araD139 Δ(ara-leu)7696 galE15 galK16 Δ(lac) X74 rpsL (StrR) hsdR2 (rK–mK+) mcrA mcrB1) (Casadaban, M. J. & Cohen, S. N. (1980) *J. Mol. Biol.*, 138, 179-207). All plasmid constructs utilize pBAD33 (Cm$^r$) (Guzman et al. (1995) *J. Bacteriol.*, 177, 4121-4130), with the promoter araBAD operon and the p15A origin of replication (low-copy number). KOD HOT START DNA polymerase (Novagen) was used for PCRs. Primers were from Operon, restriction enzymes (New England BioLabs), streptavidin-R-phycoerythrin (SA-PE) (Molecular Probes), streptavidin-coated magnetic microbeads (MYONE streptavidin T1) (Invitrogen). Qiagen mini-preps and gel extraction kits were used for DNA preparation. Ni-NTA agarose for protein purification was from Qiagen and B-PER II bacterial protein extraction reagent was from Pierce Biotechnology.

Vector and Library Construction

Construction of circularly permutated OmpX (CPX) was described previously (Rice et al. (2006) *Protein Sci*, 15, 825-836). To monitor the display level, a streptavidin binding peptide was fused to the N-terminus of CPX as described earlier; this plasmid is termed pB33CPX-SApep. To generate the libraries that join the original N- and C-termini of OmpX with 3-6 random residues, PD1237-1240 was used as the reverse primer, and PD179 as the forward primer, with pB33CPX-SApep as the template. The random positions were encoded using NNK codons allowing for all amino acids and the amber stop codon. The product of the PCR reaction was gel purified then used as a forward primer for the next reaction, using PD180 as a reverse primer, and again with pB33CPX-phage as the template. The product was then gel purified, digested with SfiI, and gel purified again. The digested insert was ligated into the similarly digested vector pB33CPX-SApep. Ligation products were desalted and electroporated into electro-competent MC1061 yielding $7.5 \times 10^7$, $7.5 \times 10^7$, $1.5 \times 10^8$, $5.0 \times 10^8$ transformants respectively.

To create the second generation library (CPX-directed), primers PD1282 with PD179 was used to randomize positions A165 and G166 using pB33CPX-SApep as the template. The product was then used as a template for PCR with PD1281 and PD179, adding the second genertion library residues. The primer encoded for G at the first position of the linker and used a restricted codon of MRM to encode for residues RKSHQN (SEQ ID NO:40) at position 3 and 6 of the linker, the remaining positions used NNK. The product of the previous PCR reaction was then used as a forward primer for the next reaction, using PD180 as a reverse primer, and again with pB33CPX-SApep as the template. The product was then digested and ligated into the similarly digested vector pB33CPX-SApep. Ligation products were desalted and electroporated into electro-competent MC1061 yielding $1.0 \times 10^9$ transformants. The various binding peptides were fused to the N-terminus of CPX and eCPX using a linker of GGQSGQ (SEQ ID NO:28). PCR was used with pB33CPX-SApep as the template, PD180 as the reverse primer, and with forward primers PD1192/PD1193 for the CRP binding peptide (EWACNDRGFNCQLQR, SEQ ID NO:29), and forward primers PD961/PD962 for the VEGF binding peptide (VEPNCDIHVMWEWECFERL, SEQ ID NO:30). The products were digested with SfiI and ligated into similarly digested vector and electroporated into MC1061. Primers PD1130-PD1133 were used in an assembly PCR to create the forward primer for the mini-Z-domain (FNMQQQRRFYEALHDPNLNEEQRNAKIKSIRDD, SEQ ID NO:31). This primer with PD180 and template pB33CPX-SApep was used in PCR, the product was digested with SfiI and ligated into similarly digested vector and electroporated into MC1061. The CPX-T7 (MASMTG-GQQMG, SEQ ID NO:32) was created using overlap extension PCR with the products from the PCR reaction with primers PD179/PD705 and PD180/PD706. The products were digested with SfiI and ligated into similarly digested vector and electroporated into MC1061. To transfer these peptides to eCPX the vectors containing the peptide CPX fusion was digested with PstI and KpnI, the smaller fragment was gel extracted and ligated to the similarly digested vector of eCPX, transferring the displayed peptide to the eCPX plasmid. To insert the P2 peptide (PAPSIDRSTKPPL, SEQ ID NO:33) at the C-terminus of CPX and eCPX, PCR was used with PD179 as the forward primer and primers PD950/PD951 as the reverse primers with pB33CPX-SApep at template. The primers also encodes a linker of GGQSGQ (SEQ ID NO:28) preceding the P2 peptide. The products were digested with SfiI and ligated into similarly digested vector and electroporated into MC1061. The gene is eCPX-nSApep-cP2. The streptavidin binding peptide was removed using KpnI and HindIII and ligation with a similarly cut insert that contains no N-terminally fused peptide, creating CPX-cP2.

To insert an extended linker of (GGGS)$_5$ (SEQ ID NO:34) between the streptavidin binding peptide and eCPX-P2, PCR was used with forward primer PD179 and reverse primers PD1429/PD1430/PD31 with pB33eCPX-nSApep-cP2 as template. The product was then gel extracted and used as the forward primer with PD180 as the reverse primer and pB33eCPX-nSApep-cP2 as template. The product was gel extracted and digested with SfiI and ligated to similarly digested vector. The portion after the OmpX signal sequence is now, GQGGQ (encoding a SfiI site, SEQ ID NO:35), AECHPQGPPCIEGRK (the streptavidin binding peptide, SEQ ID NO:36), (GGGS)$_5$ (the additional linker, SEQ ID NO:34), GGQSGQ (original linker, SEQ ID NO:28) followed by the S54 of eCPX with the P2 peptide on the C-terminus, the gene construct is termed eCPX-nSApep-linker-cP2.

Magnetic Selection and Screening by FACS

Magnetic selections were preformed for the first round of selection using the libraries CPX-5×, CPX-6×, and CPX-directed. An overnight culture of cells corresponding to 5× the library diversity were inoculated to LB medium containing 34 μg/mL chloramphenicol (Cm) for a final cell concentration of 0.05 OD$_{600}$, or 100 μL of overnight cultures into 5 mL LB Cm, which ever is greater. The cultures were then grown at 37° C. to 0.5 OD$_{600}$ with shaking (250 rpm), at which time the culture was moved to room temperature (22°) to equilibrate and then induced with L-arabinose to a final concentration of 0.04% (w/v). The cells were induced for 50 minutes, at room temperature, shaking (250 rpm). A volume of cells corresponding to 5× the library diversity was concentrated by centrifugation (3000×g, 4° C., 5 min) and resuspended in cold PBS to 10-30 OD$_{600}$. MYONE SA beads (Dynal) were added to a ratio of approximately one bead per four cells. Magnetic separation was used to wash the beads four times with a volume of LB equivalent to the volume used in the initial labeling, and the beads plus bound cells were finally resuspended in LB with Cm and 0.2% glucose (w/v) for overnight growth.

For flow cytometric sorting, 50 μL of overnight cultures of the libraries were inoculated to 5 mL LB Cm. Cells were induced as described in the previous paragraph, in future rounds of sorting the induction time was decreased to 30 minutes. Ten μL of cells were labeled with 100 μL of 100 nM SA-PE in PBS on ice for 45 minutes, pelleted by centrifugation, and the supernatant was removed. Cells were resuspended in ice-cold PBS at approximately $10^7$ cells/mL and immediately analyzed and sorted using a FACSARIA cytometer with 488 nm excitation. Between 1 and 5% of the most labeled cells were collected and amplified for further rounds of analysis and/or sorting by growing overnight in LB medium containing glucose and Cm. A subset of the sort was plated directly on agar for isolation of single clones. Typically 4-10 selected clones were assayed for antigen binding by flow cytometry, and the identity of each peptide insert was determined by DNA sequencing.

Clonal Characterization

To compare the display level of CPX and eCPX as a function of time of CPX and eCPX, cells were subcultured 1:50 from overnight stocks into 5 mL LB Cm and grown for 2 hours shaking (250 rpm) at 37° C. The cells were then moved to room temperature (22° C.) to equilibrate and induced with 0.04% (w/v) L-arabinose still shaking at 250 rpm. Five μL samples were taken prior to induction, 30, 60, and 90 minutes after induction then added to 50 μL of 100 nM SA-PE in PBS and incubated on ice for 45 minutes. After which the cells were centrifuged (3000 g, 5 min), supernatant removed, and resuspended in 500 μL ice cold PBS. Cells were immediately analyzed with a FACSARIA using 488 nm excitation and collected fluorescence data at 576 nm.

To compare the display of various peptides using CPX and eCPX, cultures were started using 50 μL of overnight culture in 5 mL LB Cm. Cultures expressing the mini-Z domain, SA binding peptide, P2 peptide, and T7 epitope were grown until an $OD_{600}$ of 0.4 and moved to room temperature (22°) to equilibrate and then induced with L-arabinose to a final concentration of 0.04% (w/v) for 30 minutes, and two hours for the mini-Z domain. Cultures expressing the CRP and VEGF peptides were induced at 37° C. at an of $OD_{600}$ 0.4 for 30 minutes. Five μL of induced cells were added to 50 μL of PBS containing the respective antigens at the following concentrations: YPet-Mona 50 nM, biotinylated VEGF 65 nM, biotinylated CRP 100 nM, Alexa labeled human IgG 300 nM, SA-PE 100 nM, anti-T7.tag monoclonal IgG 6.7 nM. Samples were labeled on ice for 45 minutes. Biotinylated samples were spun down at 3000 g for 5 minutes and supernatant removed. Cells were resuspended in 50 μL of PBS with 10 nM SA-PE and put on ice for 45 minutes. Before cytometric analysis samples were spun down at 3000 g for 5 minutes, supernatants removed, and 500 μL of PBS added to resuspend the cells. Samples were excited with at 488 nm, fluorescence data was collected at 576 nm for SA-PE labeled samples and 530 nm for Alexa labeled samples and YPet conjugated samples.

For the dual labeling experiments, cells were subcultured 1:50 from overnight stocks into 5 mL LB Cm and grown for 2 hours shaking (250 rpm) at 37° C. The cells were then induced with 0.04% (w/v) L-arabinose. Cells expressing eCPX-nSApep-cP2 were expressed for 25 minutes at 37° C., and cells expressing eCPX-nSApep-linker-cP2 were expressed for 45 minutes at 37° C. Five μL of cells were labeled with 50 μL of PBS with 100 nM SA-PE only, 40 nM Ypet-Mona only, or with both probes simultaneously. The cells were incubated at room temperature for 45 minutes, centrifuged at 3000 g for 5 minutes, and supernatant removed. The cells were left on ice before resuspension with 500 μL ice cold PBS and analyzed using cytometry with 488 nm excitation and measuring 576 nm and 530 nm emission.

Example 2: Circularly Permuted OmpX Libraries

The construction of a circularly permuted outer membrane protein OmpX (CPX) for use as a protein scaffold for polypeptide display was described previously (see U.S. patent application Ser. No. 10/920,244, which is herein incorporated by reference in its entirety). One of the advantages of CPX is that both the N- and C-termini are exterior to the cell, which allows polypeptides to be displayed from either terminus. The CPX protein scaffold consists of the native OmpX signal sequence, which is cleaved after translocation; a sequence with an embedded SfiI restriction site (GQSGQ) (SEQ ID NO: 35) after which peptides may be inserted; a flexible linking sequence (GGQSGQ) (SEQ ID NO:28); amino acids S54-F148 of the mature OmpX; a GGSG (SEQ ID NO:2) linker joining the native C- and N-termini; and finally, amino acids A1-S53 of the mature OmpX.

Figure 1B:
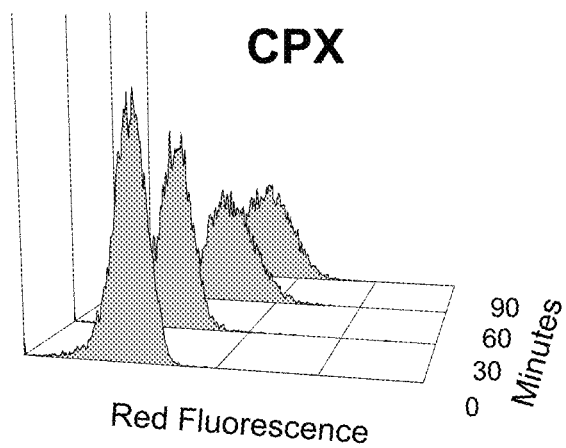

In order to assess the extent of peptide display, a disulfide constrained streptavidin binding peptide (SApep) with the following amino acid sequence, AECHPQGPPCIEGRK (SEQ ID NO:36) (Giebel et al. (1995) *Biochemistry*, 34, 15430-15435), was fused to the N-terminus of CPX allowing cell labeling using a fluorescently-conjugated streptavidin probe and measurement of display levels using cytometry. CPX yielded a reduced level of peptide display when compared to cells displaying the same peptide presented as an insertion within the corresponding region of OmpX (FIGS. 1A, 1B). This reduced display level has the drawback that longer induction periods are required to allow for sufficient fluorescence labeling and library screening, thereby causing cell stress that can result in growth biases during library selection (Daugherty et al. (1999) *Protein Eng*, 12, 613-621).

The CPX scaffold was constructed using an arbitrarily chosen flexible linker (GGSG) (SEQ ID NO:2) to join the native N- and C-termini. Thus, alternative linkers and point mutations within CPX could enhance the display of peptides on the cell surface. In order to enhance the display characteristics of CPX, various regions of the transmembrane protein were targeted for mutagenesis. An optimized linker region joining the native N- and C-termini was identified by generating and screening four libraries allowing for three (3×), four (4×), five (5×), and six (6×) random residues to be inserted in place of the GGSG (SEQ ID NO:2) linker using the degenerate codon NNK. Each library was screened separately using FACS for clones exhibiting a high level of fluorescence after 50 minutes of induction, indicating increased display of SApep binding to streptavidin-R-phycoerythrin (SA-PE). Under these conditions, the parent CPX scaffold yielded display levels only slightly greater than background autofluorescence after 50 minutes of expression, making the selection of mutants more efficient. After sorting, the display level of several clones was measured using cytometry, and their sequences were determined by DNA sequencing (Table 1).

TABLE 1

Sequence Clones from Five Selected Linker Libraries

| Clone | Positions 165 | Positions 166 | Linker | Relative Display level |
|---|---|---|---|---|
| CPX | A | G | GGSG (SEQ ID NO: 2) | 2.3 [a] / 1.5 [b] |
| *Three residue linker library* | | | | |
| CPX-3X-1 | A | G | GRK (SEQ ID NO: 3) | 8.9 [a] |
| CPX-3X-2 | A | G | GRK (SEQ ID NO: 3) | 8.3 [a] |
| CPX-3X-3 | A | G | GTK (SEQ ID NO: 4) | 7.1 [a] |
| CPX-3X-4 | A | G | GKK (SEQ ID NO: 5) | 10 [a] |
| *Four residue linker library* | | | | |
| CPX-4X-1 | A | G | GSKR (SEQ ID NO: 6) | 18 [a] |
| CPX-4X-2 | A | G | GRQK (SEQ ID NO: 7) | 14 [a] |
| CPX-4X-3 | A | G | SWPN (SEQ ID NO: 8) | 15 [a] |
| CPX-4X-4 | V | G | PRKS (SEQ ID NO: 9) | 22 [a] |
| *Five residue linker library* | | | | |
| CPX-5X-1 | A | G | GRTRK (SEQ ID NO: 10) | 24 [a] |
| CPX-5X-2 | A | G | GRKRN (SEQ ID NO: 11) | 22 [a] |
| CPX-5X-3 | V | G | GATRR (SEQ ID NO: 12) | 32 [a] |
| CPX-5X-4 | A | S | GSQSK (SEQ ID NO: 13) | 36 [a] |
| *Six residue linker library* | | | | |
| CPX-6X-1 | A | G | GTKRYH (SEQ ID NO: 14) | 35 [a] |
| CPX-6X-2 | A | G | GRRHYK (SEQ ID NO: 15) | 28 [a] |
| CPX-6X-3 | A | G | GNRRHR (SEQ ID NO: 16) | 24 [a] |
| CPX-6X-4 | A | S | GSKQSK (SEQ ID NO: 17) | 38 [a] |
| *Second generation library* | | | | |
| CPX-L2-1 | L | S | GSKSRR (SEQ ID NO: 18) | 33 [b] |
| CPX-L2-2 | F | S | GRKNSH (SEQ ID NO: 19) | 19 [b] |
| CPX-L2-3 | I | S | GTRGSQ (SEQ ID NO: 20) | 29 [b] |
| CPX-L2-4 | L | S | GHRSHR (SEQ ID NO: 21) | 27 [b] |
| CPX-L2-5 | I | S | GDRKRR (SEQ ID NO: 22) | 28 [b] |
| CPX-L2-6 | V | A | GARGRH (SEQ ID NO: 23) | 24 [b] |
| CPX-L2-7 | V | S | GTHNSQ (SEQ ID NO: 24) | 26 [b] |
| CPX-L2-8 | V | S | GPNKSR (SEQ ID NO: 25) | 17 [b] |
| CPX-L2-9 | I | S | GPHNSR (SEQ ID NO: 26) | 23 [b] |
| CPX-L2-10 | I | S | HRGYHAQR (SEQ ID NO: 27) | 33 [b] |

[a] Fold fluorescence above background after 50 minutes of expression
[b] Fold fluorescence above background after 25 minutes of expression Isolated clones exhibited three to fifteen-fold enhanced display compared to CPX after only a 30 minute induction period. The identified linker sequences exhibited a preference for basic residues, and glycine was present at the first position of the linker in 14 of 16 clones characterized. In addition, four of the clones had mutations preceding the native C-terminus; two with the substitution A165V and two others with G166S. These four clones were among the most efficient display scaffolds isolated. The average display level of the selected clones from each library increased with increasing linker length, and was highest for 5- and 6-mer linker clones.

In order to further enhance peptide display, the amino acid linker that joins the passenger peptide to the N-terminus of the display scaffold was also targeted for mutagenesis and screening for enhanced variants. A library was created in place of the original linking sequence GGQSGQ (SEQ ID NO:28), by randomizing these six residues. Screening yielded four clones exhibiting a ten-fold more efficient display as compared to CPX. Sequencing did not reveal a consensus within the target linker region. Instead, clones with enhanced display possessed a non-targeted mutation of either A165V or G166S. Since the randomly selected library members from the initial pool did not possess mutations outside of the intended region, these advantageous substitutions were rare and likely arose from PCR errors.

In parallel, a library was generated with random residues at the surface exposed C-terminus of CPX, since native outer membrane proteins (Omps) possess a conserved C-terminal motif that is thought to aid in Omp membrane insertion or assembly (Bos, M. P. & Tommassen, J. (2004) Curr. Opin. Microbiol., 7, 610-6). Four clones were isolated from this library that exhibited more efficient peptide display. Again, these variants did not share consensus in the randomized region, but each carried the spontaneous mutation G166S. These results suggest that the amino acid compositions of the new termini derived from circular permutation have little effect on the rate of assembly and display of CPX, whereas residues A165 and G166 play a key role in proper translocation and insertion of the protein.

Figure 2:
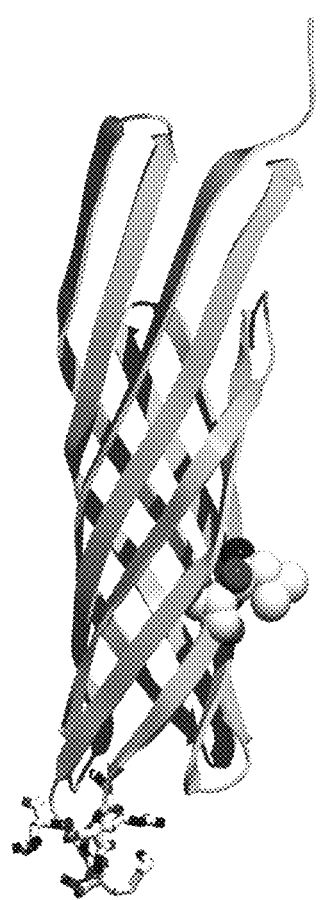
FIG. 2 depicts a model of the structure of eCPX based on the crystal structure of OmpX (Vogt, J. & Schulz, G. E. (1999) *Structure*, 7, 1301-1309). The structure shows the native N- and C-termini of OmpX joined by the six residue linker, GSKSRR (SEQ ID NO:18), the A165L and G166S mutations (shown as space filling residues), and the creation of new termini within the second extracellular loop.

In order to combine display-enhancing mutations identified within the most efficient clones from the previous libraries, a final library was designed. A six residue linker library was chosen to connect the native N- and C-termini because the longer linker typically allowed more rapid display as compared to the five residue linker (Table 1). The first amino acid of the linker was fixed to glycine since it was highly conserved in the isolated clones. The third and sixth positions were restricted to R/K/S/H/Q/N using the codon MRM, given the increased frequency of these residues at the proposed position in clones with enhanced function, and the remaining three positions were fully randomized. Positions A165 and G166, where beneficial substitutions were observed, were also fully randomized. Enhanced variants were identified using two rounds of MACS followed by two rounds of FACS, sorting clones exhibiting the highest display of the SApep after 30 minutes of induction. Ten clones were isolated after the final FACS screening (Table 1). All variant scaffolds identified possessed a more bulky hydrophobic residue (I/L/V/F) in place of alanine at position 165, a consensus for serine at position 166, and a high frequency of basic residues Arg and Lys within the linking region. The display enhancing substitutions A165/G166 are located immediately upstream of the native C-terminus of OmpX (FIG. 2).

Example 3: Expression Characteristics of Optimized CPX

Figure 1C:
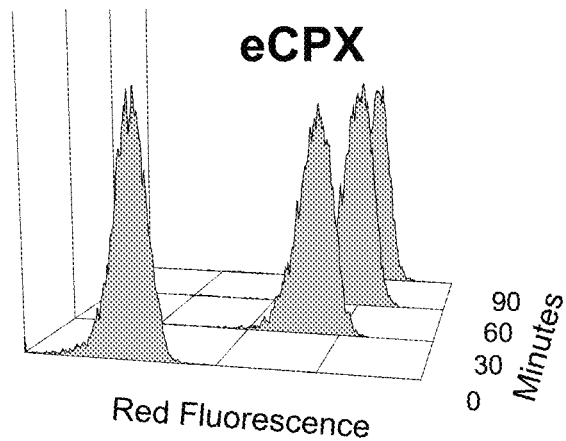

The scaffold variant exhibiting the most enhanced display characteristics, CPX-L2-1, or enhanced CPX (eCPX), was then compared to CPX and OmpX. The cell surface display level of SApep was measured at incremental times after induction of expression for these three scaffolds. This peptide was displayed either at the N-terminus (CPX and eCPX) or as an insertional fusion within the second extracellular loop of OmpX. The level of display was measured before and after 30, 60, and 90 minutes of induction using flow cytometry (FIGS. 1A-1C). The display rate of eCPX was substantially increased relative to that of CPX, and even slightly higher than that of OmpX. After only 30 minutes of expression, the level of display of eCPX-nSApep was 50-fold above background autofluorescence. Introducing A165L and G166S into OmpX resulted in nearly identical display of SApep relative to that obtained with OmpX (data not shown).

Figure 3:
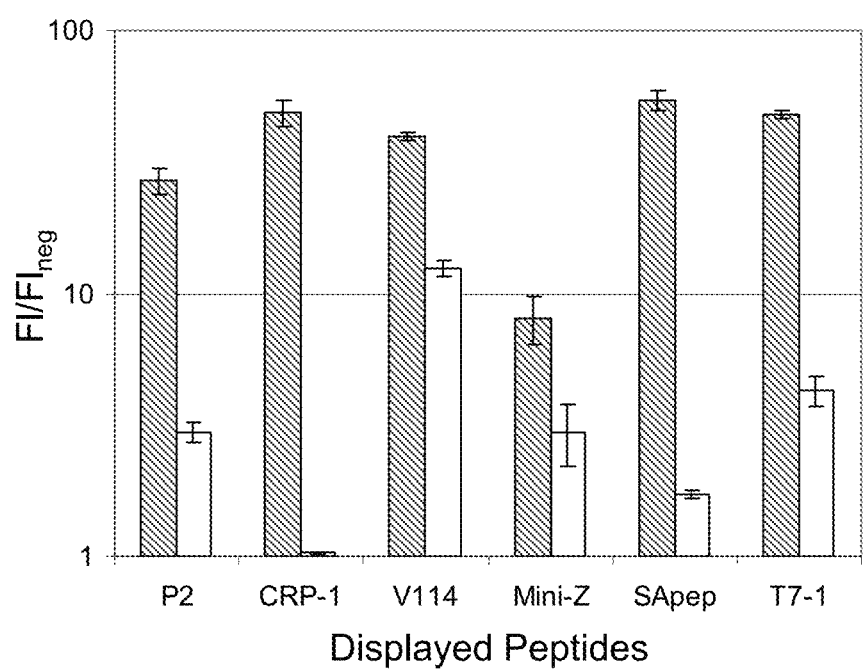
FIG. 3 is a graph depicting the display levels of various peptides and mini-proteins using eCPX (shaded) and CPX (white) measured using FACS. The x-axis indicates the fold fluorescence above background for each protein target in the corresponding fluorescent channel. P2 was labeled with mona which is fused to the fluorescent protein YPet. CRP-1 and V114, was labeled with biotinylated CRP and VEGF respectively then labeled with SA-PE. Mini-Z and T7-1 were labeled with Alexa conjugated human IgG and anti-T7.tag monoclonal IgG respectively. SApep was labeled with SA-PE.

In order to determine whether the enhanced display using the eCPX scaffold is a general effect or specific to the streptavidin binding peptide SApep, several unrelated passenger peptides were fused to the N-terminus of CPX and eCPX and their display levels were compared (FIG. 3). Surprisingly, a disulfide-constrained peptide binding to C-reactive protein (CRPpep) (EWACNDRGFNCQLQR) (SEQ ID NO:29), displayed with eCPX yielded nearly 50-fold higher florescence labeling than that for CPX, after only 30 minutes of expression. In fact, the fluorescence of cells displaying CRPpep from CPX could not be distinguished from background (FIG. 3). Similarly, the T7.tag epitope (MASMTGGQQMG) (SEQ ID NO:32) was displayed more efficiently from eCPX than from CPX. A disulfide-constrained 19-mer peptide binding to vascular endothelial growth factor (VEGF) identified previously using phage display (Fairbrother et al. (1998) *Biochemistry*, 37, 17754-17764) was also displayed over three-fold more efficiently within eCPX. Additionally, an IgG binding miniprotein (a minimized version of the Z-domain from protein A (Braisted, A. C. & Wells, J. A. (1996) *Proc. Natl. Acad. Sci. USA*, 93, 5688-5692, composed of 33-amino acids that form two antiparallel α-helices, exhibited a display level roughly three-fold higher than that from CPX after two hour induction period. Finally, P2, a proline-rich peptide (PAPSIDRSTKPPL) (SEQ ID NO:33) known to bind to the C-terminal SH3 domain of Mona (Harkiolaki, et al. 2003), was expressed as a C-terminal fusion using both CPX and eCPX. Similar to the increased efficiency of display at the N-terminus, the display level after only 30 minutes of expression of P2 using eCPX was improved by ninefold compared to display with CPX. Thus, for all peptides investigated, the eCPX scaffold increased display levels when compared to the parental CPX.

Example 4: Biterminal Display with eCPX

Two distinct peptides were simultaneously displayed on the structurally adjacent N- and C-termini of eCPX. SApep was fused to the N-terminus, and the P2 peptide fused to the C-terminus (eCPX-nSApep-cP2). Labeling with fluorescent probes SA-PE (red) and YPet-Mona (Nguyen, A. W. & Daugherty, P. S. (2005) *Nat. Biotechnol.*, 23, 355-360) (green) enabled independent detection of each peptide using flow cytometry. To determine the ability for eCPX to simultaneously display these two peptides, cells expressing the biterminal display scaffold were labeled with SA-PE only, YPet-Mona only, or both probes concurrently. If the peptides bind to their respective receptors independently (i.e., without any steric clashes), there should not be a difference between the extent of single color labeling (fluorescence intensity) of the sample labeled with one probe and that labeled with both fluorescent probes simultaneously.

Figure 4A:
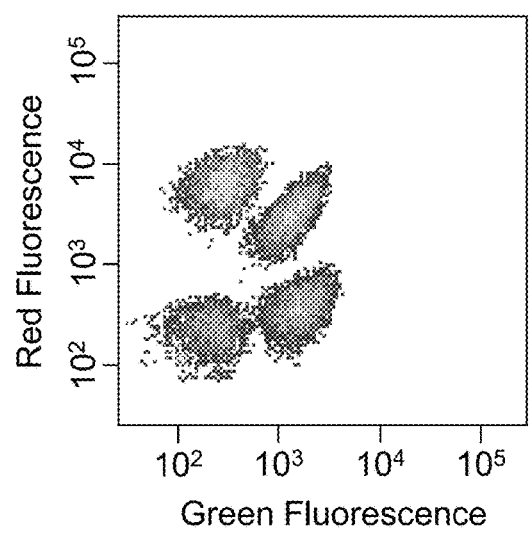
FIGS. 4A and 4B, show an overlay of 2-D cytometry data of eCPX displaying SApep on the N-terminus and P2 on the C-terminus with a six (FIG. 4A) and a twenty-six (FIG. 4B) residue linker connecting SApep to the N-terminus. In both plots; negative control (bottom left population), cells labeled with only SA-PE (top left population), cells labeled with SA-PE and YPet-mona (top right population), cells labeled with only YPet (bottom right population). Display using the longer linker allows for more efficient simultaneous labeling of both termini.
Figure 4B:
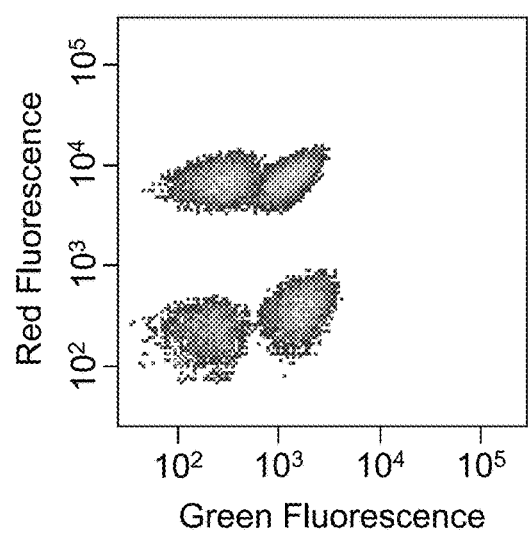

However, simultaneous labeling of cells expressing a fusion protein of the form N'-SApep-eCPX-P2-C' with SA-PE and YPet-Mona, or with each probe separately, yielded differing extents of labeling, consistent with steric interference between these two large fluorescent probes (290 kD and 34 kD, respectively). Specifically, the fluorescence of the cells when labeled with only one probe was always greater than the fluorescence in the corresponding channel of the cells when labeled with both probes simultaneously. In an attempt to reduce steric interference, a long flexible linker of the form $(GGGS)_5$ (SEQ ID NO:34) was inserted between SApep and eCPX, resulting in a total linker length of 26 amino acids causing SApep to be further from the cell surface and thus increasing the distance between the two peptides. Using this long linker, independent labeling of each displayed peptide was enhanced (FIG. 4).

These results indicate that the use of a long, unstructured linker can increase the accessibility of large proteins to peptides simultaneously displayed at both termini of eCPX, without substantially reducing the level of display.

Thus, in order to identify CPX scaffold variants with optimal linker sequences for joining the native C- and N-termini of OmpX, four separate libraries with three, four, five or six random linker amino acids were screened using MACS and FACS. Enhanced variants revealed a preference for longer linkers of five to six residues, a strict consensus for glycine at the first position of the linker, and an abundance of basic residues in the remaining positions. Substitutions (A165V, G166S) near the native C-terminus of OmpX greatly increased the display level, and probably arose from rare errors introduced during PCR which were enriched from the large libraries ($10^9$). Based on enhanced variants from the initial libraries, a final library was designed with a six residue linker that included restricted positions based on the previous selections and a randomization of positions A165 and G166. After screening, the variant exhibiting the most improvement in display characteristics was named eCPX, and carried substitutions A165L and G166S, with a linker sequence of GSKSRR (SEQ ID NO:18).

The eCPX variant has been shown to increase the display rate of various polypeptide insertions, on either the N- or C-terminus as compared to the parental CPX. This allows for library screens to be more efficient and less biased towards peptides that are difficult to display.

Also, eCPX has the flexibility to display peptides on either the N- or C-terminus, which is important for many protein binding interactions such as PDZ domains, which preferentially interact with C-terminal peptides (Harris, B. Z. & Lim, W. A. (2001) *J. Cell Sci.,* 114, 3219-3231).

In addition to displaying single peptides on one terminus, two peptides can be displayed simultaneously on opposite termini of eCPX. This biterminal display has numerous advantages including the ability to quantify to the amount of eCPX displayed on the cell surface or allow for a screen of libraries on both termini simultaneously. To validate biterminal display, a variant of eCPX displaying N-terminal SApep and C-terminal P2pep, labeled simultaneously with two different protein targets demonstrated that dual labeled cells had similar fluorescent levels as individually labeled cells in the corresponding channels when longer linkers were inserted to avoid steric hindrances of binding both proteins in close proximity. The quantification of the display level during library screening by labeling of a C-terminal peptide such as P2pep allows for peptides with a high affinity but low display level to be differentiated from peptides with a high display but moderate affinity. Moreover, biterminal display allows for the possibility of creating peptide libraries on each terminus where both peptides can bind to separate regions of the same protein target, causing increased binding affinity and specificity through avidity.

The molecular engineering of eCPX has created a circularly permuted transmembrane protein that has both termini facing the exterior of the cell and inserts into the outer membrane as efficiently as the non-permuted variant. The amino acid sequence used to join the termini played a major role in the proper function of CPX, and minor changes elsewhere in the protein aided in display of peptides using eCPX. This knowledge can be applied to improve other circularly permuted proteins to create variants that are as stable as the wild-type variant but with the termini at a chosen position. Moreover, this unique protein scaffold allows for multiple possibilities for the display of polypeptides and engineering the surface of *E. coli.* and has advanced the robustness of bacterial surface display.

Thus, methods for bacterial display of proteins and peptides using circularly permuted OmpX (CPX) variants containing optimized linkers and selected mutations at positions 165 and 166 are disclosed. Although preferred embodiments of the subject invention have been described in some detail, it is understood that obvious variations can be made without departing from the spirit and the scope of the invention as described herein.

What is claimed is:

1. A circularly permuted OmpX (CPX) variant comprising a linker joining the native N-terminus and native C-terminus of OmpX,
    wherein the CPX variant comprises a non-native N-terminus and a non-native C-terminus,
    wherein the linker is 4-8 residues in length and comprises a sequence X-Zn,
    wherein X is an amino acid selected from the group consisting of: serine, threonine, and proline,
    wherein each Z is independently any amino acid, and n is 2 to 4, and
    wherein at least one of the Z residues is independently selected from the group consisting of: lysine, arginine, glutamine, asparagine, or histidine.

2. The CPX variant of claim 1, wherein the first residue of the linker is a glycine.

3. The CPX variant of claim 1, wherein the linker comprises at least two basic residues.

4. The CPX variant of claim 1, wherein the linker comprises two arginine residues.

5. The CPX variant of claim 1, wherein the linker comprises two lysine residues.

6. The CPX variant of claim 1, wherein the linker comprises at least one arginine residue and at least one lysine residue.

7. The CPX variant of claim 1, wherein the linker is 5 residues in length.

8. The CPX variant of claim 1, wherein the linker is 6 residues in length.

9. The CPX variant of claim 8, wherein the first residue of the linker is a glycine and the third and sixth residues of the linker are selected from the group consisting of arginine, lysine, serine, histidine, glutamine, and asparagine.

10. The CPX variant of claim 1, comprising one or more mutations that increase the display efficiency of a passenger peptide compared to the CPX variant in the absence of the mutations, wherein at least one mutation is at a position corresponding to A165 or G166 of the native OmpX protein consisting of SEQ ID NO:1.

11. The CPX variant of claim 10, comprising one or more mutations selected from the group consisting of an A165V mutation, an A165L mutation, an A165I mutation, an A165F mutation, a G166S mutation, a G166A mutation and combinations thereof.

12. The CPX variant of claim 1, comprising a passenger polypeptide fused to the non-native N-terminus of the CPX variant.

13. The CPX variant of claim 12, comprising a linker between the non-native N-terminus of the CPX variant and the passenger polypeptide.

14. The CPX variant of claim 1, comprising a passenger polypeptide fused to the non-native C-terminus of the CPX variant.

15. The CPX variant of claim 14, comprising a linker between the non-native C-terminus of the CPX variant and the passenger polypeptide.

16. The CPX variant of claim 1, comprising a first passenger polypeptide fused to the non-native N-terminus of the CPX variant and a second passenger polypeptide fused to the non-native C-terminus of the CPX variant.

17. The CPX variant of claim 16, wherein the first passenger polypeptide or the second passenger polypeptide comprises a detectable label.

18. The CPX variant of claim 17, wherein both the first passenger polypeptide and the second passenger polypeptide comprise detectable labels.

19. The CPX variant of claim 18, wherein the first passenger polypeptide comprises a different detectable label than the second passenger polypeptide.

20. The CPX variant of claim 16, comprising a linker between the first passenger polypeptide and the non-native N-terminus of the CPX variant or the second passenger polypeptide and the non-native C-terminus of the CPX variant.

21. The CPX variant of claim 20, wherein the linker between the first passenger polypeptide and the non-native N-terminus of the CPX variant or between the second passenger polypeptide and the non-native C-terminus of the CPX variant comprises a sequence selected from the group consisting of SEQ ID NO:28 and SEQ ID NO:34.

22. The CPX variant of claim 13, wherein the linker between the non-native N-terminus of the CPX variant and the passenger polypeptide comprises a sequence selected from the group consisting of SEQ ID NO:28 and SEQ ID NO:34.

23. The CPX variant of claim 15, wherein the linker between the non-native C-terminus of the CPX variant and the passenger polypeptide comprises a sequence selected from the group consisting of SEQ ID NO:28 and SEQ ID NO:34.

24. The CPX variant of claim 1, wherein 2 or 3 of the Z residues are independently selected from the group consisting of: lysine, arginine, glutamine, asparagine, or histidine.

25. The CPX variant of claim 24, comprising one or more mutations that increase the display efficiency of a passenger peptide compared to the CPX variant in the absence of the mutations, wherein at least one mutation is at a position corresponding to A165 or G166 of the native OmpX protein consisting of SEQ ID NO:1.

26. The CPX variant of claim 25, comprising one or more mutations selected from the group consisting of an A165V mutation, an A165L mutation, an A165I mutation, an A165F mutation, a G166S mutation, a G166A mutation and combinations thereof.

27. The CPX variant of claim 24, comprising a passenger polypeptide fused to the non-native N-terminus of the CPX variant.

28. The CPX variant of claim 27, comprising a linker between the non-native N-terminus of the CPX variant and the passenger polypeptide, wherein said linker comprises a sequence selected from the group consisting of SEQ ID NO:28 and SEQ ID NO:34.

29. The CPX variant of claim 24, comprising a passenger polypeptide fused to the non-native C-terminus of the CPX variant.

30. The CPX variant of claim 29, comprising a linker between the non-native C-terminus of the CPX variant and the passenger polypeptide, wherein said linker comprises a sequence selected from the group consisting of SEQ ID NO:28 and SEQ ID NO:34.

31. A method of making a polypeptide display library, the method comprising:
provetiding a plurality of expression vectors expressing CPX variants of claim 1 carrying a plurality of passenger polypeptides;
transfecting bacterial cells with said expression vectors; and
culturing the bacterial cells under conditions that permit expression of said passenger polypeptides on the surface of the bacterial cells.

32. A method of screening for a CPX variant that displays a passenger polypeptide with greater efficiency than another carrier protein carrying the same passenger polypeptide, the method comprising:
transfecting a bacterial cell with an expression vector expressing a CPX variant of claim 1 carrying the passenger polypeptide;
screening for display of the passenger polypeptide at the surface of the bacterial cell within 25 minutes after inducing the expression of the CPX variant carrying the passenger polypeptide; and
comparing the display efficiency of the CPX variant carrying the passenger polypeptide to the display efficiency of another carrier protein carrying the same passenger polypeptide expressed under the same conditions.

33. A method of enhancing the display efficiency of a passenger polypeptide, the method comprising:
screening a plurality of different CPX variants of claim 1; and
selecting the CPX variant that displays the passenger polypeptide with the greatest efficiency compared to the plurality of other CPX variants.

34. A method of screening a library of polypeptides for the ability to bind to a target molecule, the method comprising:
a) providing a polypeptide display library comprising CPX variants of claim 1 carrying a plurality of passenger polypeptides displayed on bacterial cells,
b) contacting the plurality of passenger polypeptides with the target molecule, and
c) identifying at least one displayed passenger polypeptide that binds to the target molecule.

35. The method of claim 34, wherein the target molecule is selected from the group consisting of a receptor, a ligand, an antibody, an antigen, an enzyme, a transporter, a substrate, an inhibitor, an activator, a cofactor, a drug, a nucleic acid, a lipid, a carbohydrate, a glycoprotein, a small organic molecule, and an inorganic molecule.

36. The method of claim 34, wherein said target molecule comprises a detectable label, wherein identifying the target molecule bound to at least one passenger polypeptide comprises detecting the label attached to said target molecule.

37. A method of screening a library of polypeptides for biological activity in the presence of a target molecule, the method comprising:
a) providing a polypeptide display library comprising CPX variants of claim 1 carrying a plurality of passenger polypeptides displayed on bacterial cells,
b) contacting the plurality of passenger polypeptides with the target molecule,
c) assaying for biological activity in the presence of the target molecule, and
d) identifying at least one displayed passenger polypeptide that has biological activity.

38. The method of claim 37, wherein the biological activity is enzymatic activity, substrate activity, ligand-binding activity, transport activity, agonist activity, or antagonist activity.

39. The method of claim 37, wherein the target molecule is selected from the group consisting of a receptor, a ligand, an antibody, an antigen, an enzyme, a transporter, a substrate, an inhibitor, an activator, a cofactor, a drug, a nucleic acid, a lipid, a carbohydrate, a glycoprotein, a small organic molecule, and an inorganic molecule.

* * * * *